US007488484B2

(12) United States Patent
Weiner et al.

(10) Patent No.: US 7,488,484 B2
(45) Date of Patent: Feb. 10, 2009

(54) NUCLEIC ACID EXPRESSION CASSETTE ENCODING AN HIV POLYPROTEIN COMPRISING THE ANCILLARY GENE PRODUCTS VIF, VPU, AND NEF

(75) Inventors: David B. Weiner, Merion Station, PA (US); Velpandi Ayyavoo, Pittsburgh, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 788 days.

(21) Appl. No.: 10/312,197

(22) PCT Filed: Jul. 12, 2001

(86) PCT No.: PCT/US01/41357

§ 371 (c)(1),
(2), (4) Date: May 16, 2003

(87) PCT Pub. No.: WO02/06303

PCT Pub. Date: Jan. 24, 2002

(65) Prior Publication Data

US 2004/0106100 A1    Jun. 3, 2004

Related U.S. Application Data

(60) Provisional application No. 60/218,192, filed on Jul. 14, 2000.

(51) Int. Cl.
*A61K 39/21* (2006.01)
*A61K 39/295* (2006.01)
*A62K 39/00* (2006.01)

(52) U.S. Cl. ............... 424/208.1; 424/192.1; 424/202.1

(58) Field of Classification Search ............. 536/29.72; 424/188.1, 208.1
See application file for complete search history.

(56) References Cited

U.S. PATENT DOCUMENTS

| | | | |
|---|---|---|---|
| 4,722,848 A | 2/1988 | Paoletti et al. |
| 4,736,866 A | 4/1988 | Leder et al. |
| 4,873,191 A | 10/1989 | Wagner et al. |
| 5,017,487 A | 5/1991 | Stunnenberg et al. |
| 5,077,044 A | 12/1991 | Stocker |
| 5,110,587 A | 5/1992 | Paoletti et al. |
| 5,112,749 A | 5/1992 | Brey et al. |
| 5,174,993 A | 12/1992 | Paoletti et al. |
| 5,223,424 A | 6/1993 | Cochran et al. |
| 5,225,336 A | 7/1993 | Paoletti |
| 5,240,703 A | 8/1993 | Cochran |
| 5,242,829 A | 9/1993 | Gritz et al. |
| 5,294,441 A | 3/1994 | Curtiss, III |
| 5,294,548 A | 3/1994 | McLinden et al. |
| 5,310,668 A | 5/1994 | Ellis et al. |
| 5,387,744 A | 2/1995 | Curtiss, III |
| 5,389,368 A | 2/1995 | Curtiss, III |
| 5,424,065 A | 6/1995 | Curtiss, III |
| 5,453,364 A | 9/1995 | Paoletti et al. |
| 5,462,734 A | 10/1995 | Letchworth, III |
| 5,470,734 A | 11/1995 | Sondermeijer |
| 5,482,713 A | 1/1996 | Paoletti |
| 5,593,972 A | 1/1997 | Weiner et al. |
| 5,739,118 A | 4/1998 | Carrano et al. |
| 5,830,876 A | 11/1998 | Weiner et al. |
| 5,837,533 A | 11/1998 | Boutin |
| 6,043,081 A | 3/2000 | Cohen et al. |

FOREIGN PATENT DOCUMENTS

| | | |
|---|---|---|
| WO | WO99/43839 | 9/1999 |
| WO | WO 02/04493 | 1/2002 |

OTHER PUBLICATIONS

Ayyavoo, V., et al., 2000, Immunogencity of a novel DNA vaccine cassette expressing multiple human immunodeficiency virus (HIV-1) accesory genes, AIDS 14:1-9.*

Burton, D. R., et al., 2004, HIV vaccine design and the neutralizing antibody problem, Nat. Immunol. 5(3):233-236.*

Desrosiers, R. C., 2004, Prospects for an AIDS vaccine, Nat. Med. 10(3):221-223.*

Desrosiers, R. C., 1999, Strategies used by human immunodeficiency virus that allow persistent viral replication, Nat. Med. 5(7):723-725.*

Burton, D. R., and J. P. Moore, 1998, Why do we not have an HIV vaccine and how can we make one?, Nat. Med. Vaccine Suppl. 4(5):495-498.*

Heilman, C. A., and D. Baltimore, 1998, HIV vaccines-where are we going?, Nat. Med. Vaccine Suppl. 4(5):532-534.*

Letvin, N. L., 2006, Progress and obstacles in the development of an AIDS vaccine, Nat. Rev. Immunol. 6:930-939.*

Burton, D. R., 2002, Antibodies, viruses, and vaccines, Nat. Rev. Immunol. 2:706-713.*

Sato, et al., "Identification and localization of vpr gene product of hman immunodeficiency virus type 1," Virus Genes (1990) 4:303-312.

(Continued)

*Primary Examiner*—Jeffrey S Parkin
(74) *Attorney, Agent, or Firm*—Pepper Hamilton LLP; Mark DeLuca, Esq.

(57) ABSTRACT

Improved vaccines and methods of using the same are disclosed. Immunosuppressive compositions for treating individuals who have autoimmune diseases or transplants and methods of using the same are disclosed.

14 Claims, 9 Drawing Sheets

OTHER PUBLICATIONS

Willey, et al., "Human immunodeficiency virus type 1 Vpu protein induces rapid degradation of CD4," J. Virol. (1992) 66:7193-7200.

Ayyavoo, et al., "Development of genetic vaccines for pathogenic genes: construction of attenuated vif DNA immunization casettes," AIDS (1997) 11:1433-1444.

Merrifield, et al., "Solid phase peptide synthesis. I. The synthesis of a tetrapeptide," J. Am. Chem. Soc. (1963) 85:2149-2154.

International Search Report dated May 2, 2002 for International Application No. PCT/US01/41357.

Ayyavoo et al., "Immunogenicity of a novel DNA vaccine cassette expressing multiple human immunodeficiency virus (HIV-1) accessory genes," *AIDS* (2000) 14(1):1-9.

Supplementary Partial European Search Report dated Apr. 19, 2005 for EP Application No. 01 96 2300.

* cited by examiner

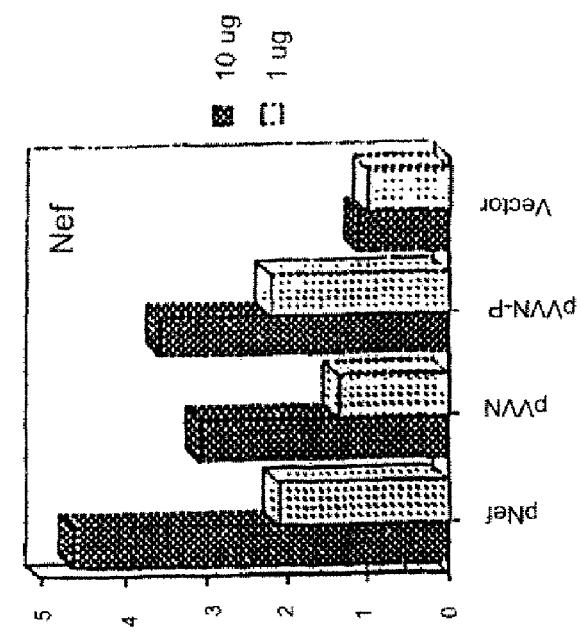
FIGURE 4A FIGURE 4B FIGURE 4C

FIGURE 6A
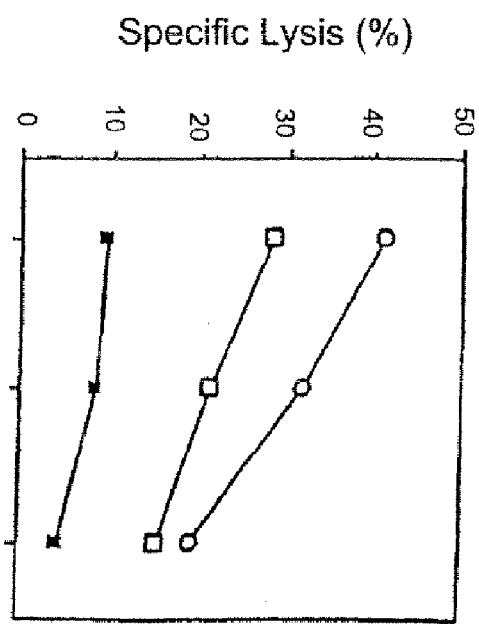
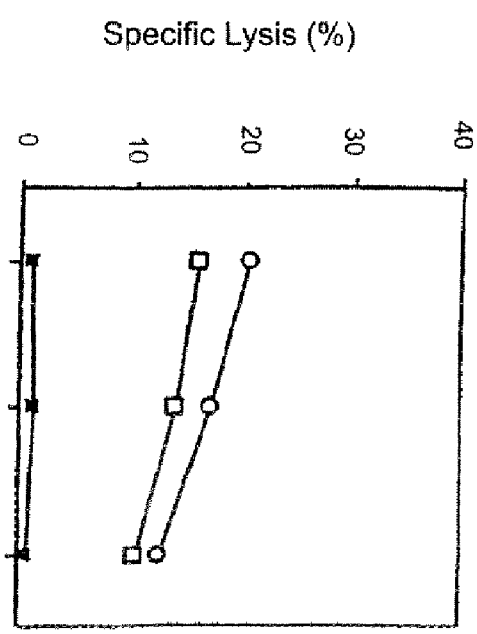

```
                          SEQUENCE LISTING

<160> NUMBER OF SEQ ID NOS: 10

<210> SEQ ID NO 1
<211> LENGTH: 580
<212> TYPE: DNA
<213> ORGANISM: Homo sapiens

<400> SEQUENCE: 1
atggaaaaca gatggcaggt gatgattgtg tggcaagtag acaggatgag gattaacaca      60
tggaaaagat tagtaaaaca ccatatgtat atttcaagga aggctaagga ctggtttat     120 agacatcact atgaaagtac taatccaaaa ataagttcag aagtacacat cccactaggg    180
gatgctaaat tagtaataac aacatattgg ggtctgcata caggagaaag agactggcat    240
ttgggtcagg gagtctccat agaatggagg aaaaagagat atagcacaca agtagaccct    300
gacctagcag accaactaat tcatctgcac tatttgatt gttttcaga atctgctata    360 agaaatacca tattaggacg tatagttagt cctaggtgtg aatatcaagc caggacataa    420
caaggtagga tctctacagt acttggcact agcagcatta taaaaccaa aacagataaa    480 gccacctttg cctagtgtta ggaaactgac agaggacaga tggaacaagc cccagaagac    540
caagggccac agagggagcc atacaatgaa tggacactac                          580

<210> SEQ ID NO 2
<211> LENGTH: 245
<212> TYPE: DNA
<213> ORGANISM: Homo sapiens

<400> SEQUENCE: 2
atgcaaccta taatagtagc aatagtagca ttagtagtag caataataat agcaatagtt     60
gtgtggtcca tagtaatcat agaatatagg aaaatattaa gacaaagaaa atagacaggt    120
taattgatag actaatagaa ggagcagaag acagtggcaa tgagagtgaa ggagaagtat    180
cagcacttgt ggagatgggg gtggaaatgg ggcaccatgc tccttgggat attgatgatc    240
tgtac                                                                245
```

<210> SEQ ID NO 3
<211> LENGTH: 620
<212> TYPE: DNA
<213> ORGANISM: Homo sapiens

<400> SEQUENCE: 3

```
atgggtggca agtggtcaaa aagtagtgtg attggatggc ctgctgtaag ggaaagaatg      60
agacgagctg agccagcagc agatgggtgg gagcagtatc tcgagaccta gaaaaacatg     120
gagcaatcac aagtagcaat acagcagcta acaatgctgc ttgtgcctgg ctagaagcac     180
aagaggagga agaggtgggt tttccagtca cacctcaggt acctttaaga ccaatgactt     240
acaaggcagc tgtagatctt agccactttt taaaagaaaa ggggggactg aagggctaa      300
ttcactccca aagaagacaa gatatccttg atctgtggat ctaccacaca caaggctact     360
tccctgattg gcagaactac acaccagggc caggggtcag atatccactg acctttggat     420
ggtgctacaa gctagtacca gttgagccag ataaggtaga agaggccaat aaaggagaga     480
acaccagctt gttacaccct gtgagcctgc atggaatgga tgaccctgag agagaagtgt     540
tagagtggag gtttgacagc cgcctagcat ttcatcacgt ggcccgagag ctgcatccgg     600
agtacttcaa gaactgctga                                                620
```

<210> SEQ ID NO 4
<211> LENGTH: 8
<212> TYPE: PRT
<213> ORGANISM: Homo sapiens

<400> SEQUENCE: 4

Arg Glu Lys Arg Ala Val Val Gly
1               5

<210> SEQ ID NO 5
<211> LENGTH: 30
<212> TYPE: DNA
<213> ORGANISM: Homo sapiens

<400> SEQUENCE: 5

```
attgaaagct tatggaaaac agatggcagg                                       30
```

<210> SEQ ID NO 6
<211> LENGTH: 36
<212> TYPE: DNA
<213> ORGANISM: Homo sapiens

<400> SEQUENCE: 6

```
tactattata ggttgcatct cgtgtccatt cattgt                                36
```

<210> SEQ ID NO 7
<211> LENGTH: 30
<212> TYPE: DNA
<213> ORGANISM: Homo sapiens

<400> SEQUENCE: 7

```
ggacacgaga tgcaacctat aatagtagca                                       30
```

<210> SEQ ID NO 8
<211> LENGTH: 42
<212> TYPE: DNA
<213> ORGANISM: Homo sapiens

<400> SEQUENCE: 8

-continued

```
tgaccacttg ccacccatct cgagatcatc aatatcccaa gg                42

<210> SEQ ID NO 9
<211> LENGTH: 28
<212> TYPE: DNA
<213> ORGANISM: Homo sapiens

<400> SEQUENCE: 9
ggagatgggt ggcaagtggt caaaaagt                                28

<210> SEQ ID NO 10
<211> LENGTH: 30
<212> TYPE: DNA
<213> ORGANISM: Homo sapiens

<400> SEQUENCE: 10
cgcaagcttc gatgtcagca gtctttgtag                              30
```

NUCLEIC ACID EXPRESSION CASSETTE ENCODING AN HIV POLYPROTEIN COMPRISING THE ANCILLARY GENE PRODUCTS VIF, VPU, AND NEF

CROSS REFERENCE TO RELATED APPLICATIONS

This application is a U.S. National Phase Application of PCT International Application PCT/US01/41357 which claims priority to U.S. Ser. No 60/218,192, filed Jul. 14, 2000.

FIELD OF THE INVENTION

The present invention relates to improved vaccines and methods of immunizing individuals against human immunodeficiency virus (HIV), to proteins and to nucleic acid molecules, pharmaceutical compositions comprising the same, and methods of using the same.

BACKGROUND OF THE INVENTION

An effective vaccine should confer long lasting immunity without causing any adverse side effects or reversion to disease status. Traditional vaccines have focused on the administration of live attenuated, whole killed or non-live preparations of pathogen to the host. These vaccines have proven effective in generating both protective humoral and cellular immune responses against a number of viruses. The development of vaccines against some viral pathogens is not an easy task. This task is complicated by several factors which include the pathobiology of the pathogen and the specificity of the host immune response. Recently, a novel tool for understanding the immune component involved in these interactions has become available. This tool i.e. genetic immunization or DNA vaccination is a unique resource for the effort to develop safe and functional vaccines against a wide range of pathogens.

The Human Immunodeficiency Virus Type 1 (HIV-1) is the etiological agent for the acquired immune deficiency syndrome (AIDS). HIV-1 is a lentivirus that uses RNA to transmit its message to its target cell where it is then converted to cDNA and integrated into the target cell nucleus. Due the high rate of errors in the conversion of RNA to cDNA, HIV-1 is a highly mutable virus, which makes developing a traditional vaccine against it a difficult task. Genetic immunization, in which short DNA segments as opposed to the whole viral genome are used to immunize patients, is proving to be a safe way to vaccinate against this virus. To date, DNA vaccines have been developed against HIV-1 structural, enzymatic, and accessory genes, and tested for their ability to induce immune responses in murines and primates. A few of these vaccine constructs are currently in phase I clinical trials.

The immune mechanism(s) involved in protection against HIV-1 remains unclear. Of a spectrum of various host immune responses, induction of cell-mediated immunity could be an especially important requirement of an effective HIV-1 vaccine candidate, because cellular immunity may play a critical role in viral clearance. CTLs can target not only the gene products present in the viral particle, but also all viral gene products which are expressed during viral replication. Earlier studies have shown that in HIV-1 infected patients, control of initial viremia is associated with the presence of CD8$^+$ T lymphocyte cellular responses. Additionally, HIV-1 positive long term non progressors and uninfected children born to HIV-1 infected mothers show very high CTL responses against HIV-1 proteins suggesting that obtaining CTL responses should be an important focus of anti-HIV vaccine development. Targeting immune responses against viral proteins through the development of specific CTL responses could aid in lowering viral load by destroying viral factories and thus lowering the establishment of initial viral load.

Primate lentiviral genomes contain genes encoding novel regulatory and accessory proteins in addition to their structural and enzymatic genes. The regulatory genes, tat and rev, and the accessory genes, nef, vif, vpr, vpu and vpx, are well conserved in primate lentiviruses, including HIV-1, HIV-2, and SIV. The well conserved nature of these genes implies that their protein products play a critical role in viral pathogenesis in vivo. Recent studies implicate the accessory genes in enhanced virion production and attribute them to the pathogenesis of HIV infection, both of which lend support to the notion that the accessory genes are actual vital components of HIV-1. These gene products represent 20% of the viral open reading frame and are immunogenic in vivo and are possibly less susceptible to mutagenesis, and thus they represent an important target for vaccine development. The development of DNA vaccines against HIV-1 accessory and regulatory genes is being researched, but the fact that these genes can potentially disrupt normal cellular activities adds an additional level of complexity to the development of anti-accessory gene DNA vaccines.

There is a need for vaccines against HIV. There is a need for compositions and methods which produce immune responses which can eliminate virally infected target cells from different clades.

BRIEF DESCRIPTION OF THE DRAWINGS

FIG. 1A shows data from experiments studying cytotoxic T lymphocyte activity induced by functional and attenuated vif and nef expression cassettes. FIG. 1B shows data from T cell proliferation experiments in which T cell proliferation was induced by immunization of plasmids expressing vif, vpu, vpr and nef:

FIG. 2A depicts the construction and design of vif, vpu and nef fusion protein and fusion protein with proteolytic cleavage sites as single expression cassettes. FIG. 2B shows data from the expression of VVN and VVN-P following in vitro translation using T7 system.

FIG. 3A shows data related to the expression and processing of VVN and VVN-P fusion protein in HeLa cells by immunoprecipitaion. FIG. 3B shows data related to the subcellular localization of VVN and VVN-P fusion proteins in vivo. FIG. 3C shows results of immunohistochemical analysis of VVN and VVN-P antigen expression.

FIGS. 4A, 4B and 4C shows data from experiments described in the Example relating to T cell proliferation of spleenocytes from mice immunized with pVVN and pVVN-P following recombinant Vif, Vpu and Nef in vitro stimulation.

FIGS. 6A and 6B show data from experiments described in the Example relating to Cytotoxic T lymphocyte response induced by pVVN and pVVN-P immunization against HIV-1 (T-tropic and dual-tropic) infected targets and cross lade CTL responses induced by spleenocytes isolated from mice immunized with VVN and VVN-P expression constructs. FIG. 6A shows data from experiments relating to Cytotoxic T lymphocyte response induced by pVVN and pVVN-P immunization against HIV-1 (T-tropic and dual-tropic) infected targets. FIG. 6B shows data from experiments relating to cross clade CTL responses induced by spleenocytes isolated from mice immunized with VVN and VVN-P expression constructs.

DESCRIPTION OF THE INVENTION

Figure 1A:
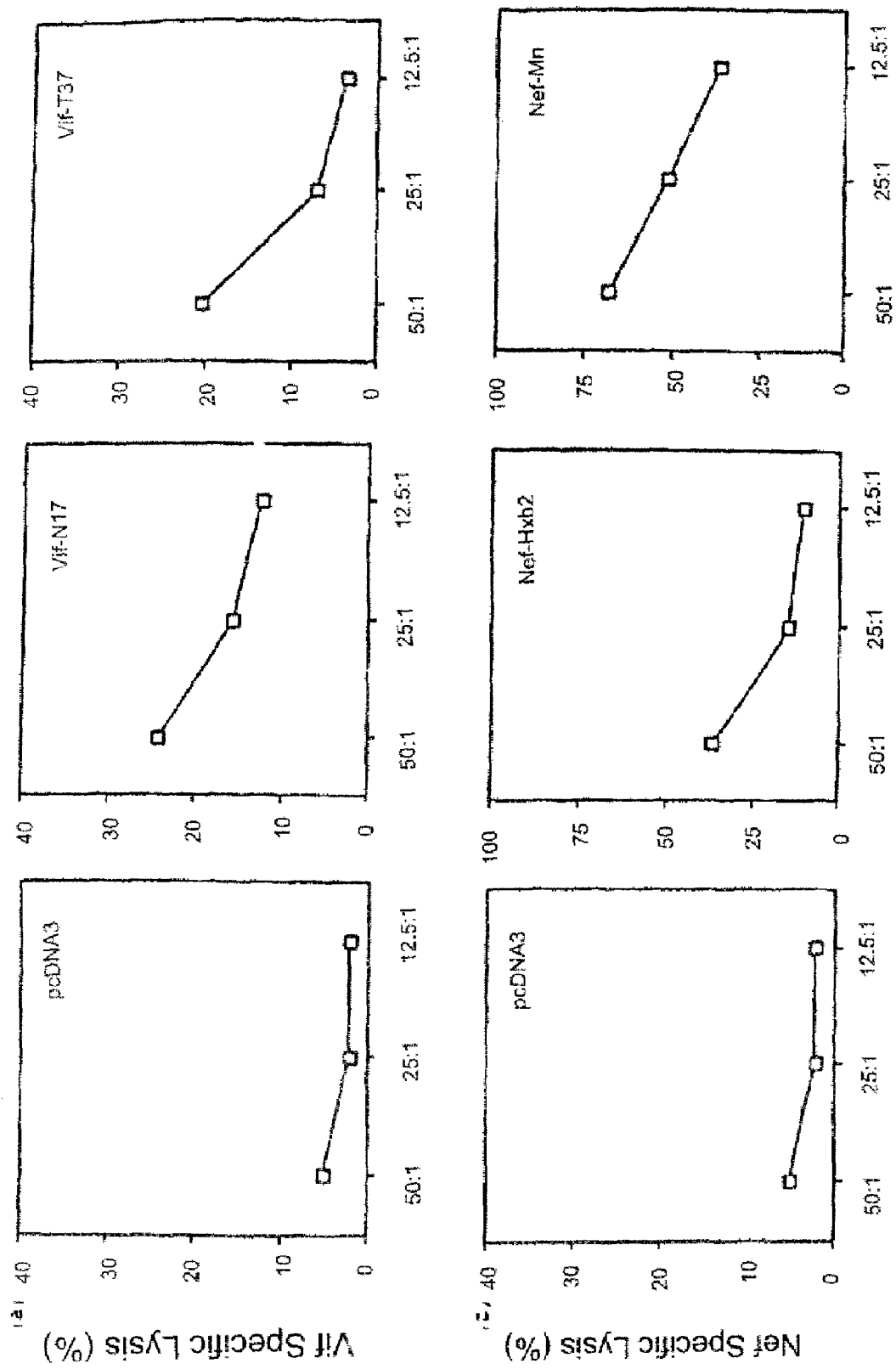
FIGS. 1A and 1B show data from experiments described in the Example.

As used herein, the term "HIV VVN polyprotein" is meant to refer to a polyprotein which includes amino acid sequences of HIV Vif, HIV Vpu and HIV Nef as a single protein. HIV VVN polyproteins include those polyproteins in which one or more of HIV Vif, HIV Vpu and HIV Nef are attenuated. HIV VVN polyproteins include those polyproteins in which HIV Vif, HIV Vpu and HIV Nef are present in any order. HIV VVN polyproteins include those polyproteins in which component protein (HIV Vif, HIV Vpu and HIV Nef) are contiguous with another component protein or separated by non component protein sequences such as but not limited to amino acid sequences which make up proteolytic cleavage sites.

As used herein, the term "HIV VVN constructs" is meant to refer to nucleic acid molecules that encode HIV VVN polyproteins.

As used herein, the term "attenuated" is meant to refer to HIV accessory proteins which are immunogenically cross reactive with wild type forms but which are non-functional or functionally impaired relative to wild type forms. Generally, attenuated proteins have modified sequences relative to functional wild type proteins. Those having ordinary skill in the art can readily identify those proteins with modified sequences that are immunogenically cross reactive with wold type forms but which are non-functional or functionally impaired relative to wild type forms.

HIV protein Vif is a 23-kD polypeptide that has been reported to be essential for thereplication of HIV in peripheral blood lymphocytes, macrophages, and certain cell lines.An assay can be performed to test Vif proteins with modified sequences to determine if the modified form is non-functional or functionally impaired relative to wild type forms. The nucleotide and amino acid sequences of HIV Vif are well known and can be accessed in Genbank and the HIV sequence database which are each incorporated herein by reference. Gene constructs that encode an attenuated HIV Vif may be produced as described in Ayyavoo V, et al(1997) AIDS 11: 1433-1444, which is incorporated herein by reference. The nucleotide sequence that encodes a preferred attenuated form of HIV Vif is SEQ ID NO: 1:

```
atgGAAAACAGATGGCAGGTGATGATTGTGTGGCAAGTAGACAG

GATGAGGATTAACACATGGAAAGATTAGTAAAACACCATATG

TATATTTCAAGGAAAGCTAAGGACTGGTTTTATAGACATCACT

ATGAAAGTACTAATCCAAAAATAAGTTCAGAAGTACACATCCC

ACTAGGGGATGCTAAATTAGTAATAACAACATATTGGGGTCTG

CATACAGGAGAAAGAGACTGGCATTTGGGTCAGGGAGTCTCCA

TAGAATGGAGGAAAAAGAGATATAGCACACAAGTAGACCCTG

ACCTAGCAGACCAACTAATTCATCTGCACTATTTTGATTGTTTT

TCAGAATCTGCTATAAGAAATACCATATTAGGACGTATAGTTA

GTCCTAGGTGTGAATATCAAGCAGGACATAACAAGGTAGGATC
```

```
-continued
TCTACAGTACTTGGCACTAGCAGCATTAATAAAACCAAAACAG

ATAAAGCCACCTTTGCCTAGTGTTAGGAAACTGACAGAGGACA

GATGGAACAAGCCCCAGAAGACCAAGGGCCACAGAGGGAGCC

ATACAATGAATGGACACtac.
```

The vif gene is isolated from a HIV-1 patient, who is asymptomatic. Functional assay such as transcomplementation studies performed and the results indicate this variant is incapable of supporting a cell-free HIV-1 infection in vitro.

HIV protein Vpu is a 16-kD polypeptide which is an integral membrane phosphoprotein that is primarily localized in the internal membranes of the cell. (Sato A., et al. Virus Genes 1990;4:303-312, which is incorporated herein by reference). In HIV infected cells, complexes are formed between the viral receptor, CD4, and the viral envelope protein in the endoplasmic reticulum causing the trapping of both proteins to within this compartment. The formation of intracellular Env-CD4 complexes thus interferes with virion assembly. Vpu liberates the viral envelope by triggering the degradation of CD4 molecules complexed with Env. (Willey R.L., et al. J Virol 1992; 66(12):7193-7200, which is incorporated herein by reference.) Vpu also increases the release of HIV from the surface of an infected cell. (Klimkait T.,etal. J Virol 1990;64:621-629, which is incorporated herein by reference.) Assays can be performed to test Vpu proteins with modified sequences to determine if the modified form is non-functional or functionally impaired relative to wild type forms. The nucleotide and amino acid sequences of HIV Vpu are well known and can be accessed in Genbank and the HIV sequence database which are each incorporated herein by reference. The nucleotide sequence that encodes a preferred attenuated form of HIV Vpu is SEQ ID NO:2:

```
atgCAACCTATAATAGTAGCAATAGTAGCATTAGTAGTAGCAAT

AATAATAGCAATAGTTGTGTGGTCCATAGTAATCATAGAATAT

AGGAAAATATTAAGACAAAGAAAAATAGACAGGTTAATTGAT

AGACTAATAGAAAGAGCAGAAGACAGTGGCAATGAGAGTGAA

GGAGAAGTATCAGCACTTGTGGAGATGGGGGTGGAAATGGGG

CACCATGCTCCTTGGGATATTGATGATCTGtac.
```

HIV protein Nef has been shown to have multiple activities, including the down regulation of the cell surface expression of CD4, (Garcia J.V. & Miller A.D. Res Virol 1992;143: 52-55, which is incorporated herein by reference) the perturbation of T-cell activation, (Luria S., et al. Proc Natl Acad Sci USA 1991;88:5326-533, which is incorporated herein by reference) and the stimulation of HIV infectivity. (Miller M.D., et al., J Exp Med 1994;179:101-113, which is incorporated herein by referenced) Assays can be performed to test Nef proteins with modified sequences to determine if the modified form is non-functional or functionally impaired relative to wild type forms. The nucleotide and amino acid sequences of HIV Nef are well known and can be accessed in Genbank and the HIV sequence database which are each incorporated herein by reference. The nucleotide sequence that encodes a preferred attenuated form of HIV Nef is SEQ ID NO:3:

```
atgGGTGGCAAGTGGTCAAAAAGTAGTGTGATTGGATGGCCTGC

TGTAAGGGAAAGAATGAGACGAGCTGAGCCAGCAGCAGATGG

GGTGGGAGCAGTATCTCGAGACCTAGAAAAACATGGAGCAATC

ACAAGTAGCAATACAGCAGCTAACAATGCTGCTTGTGCCTGGC

TAGAAGCACAAGAGGAGGAAGAGGTGGGTTTTCCAGTCACACC

TCAGGTACCTTTAAGACCAATGACTTACAAGGCAGCTGTAGAT

CTTAGCCACTTTTTAAAAGAAAAGGGGGACTGGAAGGGCTAA

TTCACTCCCAAAGAAGACAAGATATCCTTGATCTGTGGATCTA

CCACACACAAGGCTACTTCCCTGATTGGCAGAACTACACACCA

GGGCCAGGGGTCAGATATCCACTGACCTTTGGATGGTGCTACA

AGCTAGTACCAGTTGAGCCAGATAAGGTAGAAGAGGCCAATA

AAGGAGAGAACACCAGCTTGTTACACCCTGTGAGCCTGCATGG

AATGGATGACCCTGAGAGAGAAGTGTTAGAGTGGAGGTTTGAC

AGCCGCCTAGCATTTCATCACGTGGCCCGAGAGCTGCATCCGG

AGTACTTCAAGAACTGCTGA.
```

This Nef clone, which was also isolated from a long term non progressor patient, does not down modulate CD4 and MHC-I molecule upon expression in CD4 cells.

The present invention relates to polyproteins that comprise protein component sequences of human immunodeficiency virus (HIV) accessory proteins Vif, Vpu and Nef. In some embodiments, the component proteins of the polyprotein are arranged in the order from N terminal to C terminal, Vif, Vpu and Nef. In some embodiments, one or more of the protein components is an attenuated form of the accessory protein. In some embodiments, each of the human immunodeficiency virus accessory protein Vif, Vpu and Nef protein components is an attenuated form.

In some embodiments, a protease cleavage site is included between the protein components of the polyprotein. In some embodiments, a protease cleavage site is included between HIV accessory proteins Vif and Vpu. In some embodiments, a protease cleavage site is included between HI accessory proteins Vpu and Nef. In some embodiments, the component proteins of the polyprotein are arranged in the order from N terminal to C terminal, Vif, Vpu and Nef and a protease cleavage site is included between HIV accessory proteins Vif and Vpu and a protease cleavage site is included between Iv accessory proteins Vpu and Nef. In some embodiments, the protease cleavage site is REKRAVVG (SEQ ID NO:4). In some preferred embodiments, attenuated forms of the component proteins are included in the polyprotein, the component proteins of the polyprotein are arranged in the order from N terminal to C terminal, Vif, Vpu and Nef, the protease cleavage site REKRAVVG (SEQ ID NO:4) is included between Vif and Vpu and between Vpu and Nef.

The present invention relates to nucleic acid molecules which comprise coding sequences that encode polyproteins that comprise protein component sequences of HIV accessory proteins Vif, Vpu and Nef. In some embodiments, the coding sequences encode a polyprotein which the component proteins are arranged in the order from N terminal to C terminal, Vif, Vpu and Nef. In some embodiments, the coding sequences encode attenuated forms of one or more of the HIV accessory proteins Vif, Vpu and Nef. In some embodiments, the coding sequence encodes attenuated forms of each of HIV proteins Vif, Vpu and Nef. In some embodiments, the coding sequences that encode a protease cleavage site is included between the coding sequences that encode protein components of the polyprotein. In some embodiments, coding sequences that encode a protease cleavage site is included between coding sequences that encode HIV accessory proteins Vif and Vpu. In some embodiments, coding sequences that encode a protease cleavage site is included between coding sequences that encode HIV accessory proteins Vpu and Nef. In some embodiments, the coding sequences encode component proteins of the polyprotein that are arranged in the order from N terminal to C terminal, Vif, Vpu and Nef and a protease cleavage site is included between HIV accessory proteins Vif and Vpu and a protease cleavage site is included between HIV accessory proteins Vpu and Nef. In some embodiments, the coding sequences encode a protease cleavage site that is REKRAVVG (SEQ ID NO:4). In some preferred embodiments, the coding sequences encode attenuated forms of the component proteins that are included in the polyprotein, the component proteins of the polyprotein are arranged in the order from N terminal to C terminal, Vif, Vpu and Nef, and the coding sequences encodes the protease cleavage site REKRAVVG (SEQ ID NO:4) between Vif and Vpu and between Vpu and Nef.

In some embodiments, the coding sequences of the nucleic acid molecule are operably linked to regulatory elements. In some embodiments, the nucleic acid molecule is a plasmid. In some embodiments, the nucleic acid molecule is a plasmid and the coding sequences of the nucleic acid molecule are operably linked to regulatory elements.

In some embodiments, the nucleic acid molecule is included as part of or in association with a recombinant vaccine or attenuated vaccine and the coding sequences of the nucleic acid molecule are operably linked to regulatory elements.

The present invention relates to pharmaceutic compositions, including injectable pharmaceutical compositions that include the polyprotein and/or nucleic acid molecules of the invention as described above.

The present invention relates to methods immunizing individual against HIV infection. The methods comprise the step of administering a composition comprising the polyprotein and/or nucleic acid molecules of the invention as described above in an amount effective to induce a therapeutic or prophylactic immune response. In some embodiments, the individual is uninfected and the method is prophylactic. In some embodiments, the individual is infected and the method is therapeutic. Some therapeutic methods include the step of identifying individuals who are infected with HIV. Methods of identifying individuals who are infected with HIV are well known to those having ordinary skill in the art. In some embodiments, the individual is administered a poly protein. In some embodiments, the individual is administered a nucleic acid molecule that encodes the polyprotein.

According to the present invention, compositions and methods are provided which prophylactically and/or therapeutically immunize an individual against HIV. The genetic material is expressed by the individual's cells and serves as an immunogenic target against which an immune response is elicited. The resulting immune response is broad based: in addition to a humoral immune response, both arms of the cellular immune response are elicited. The methods of the present invention are useful for conferring prophylactic and therapeutic immunity. Thus, a method of immunizing includes both methods of protecting an individual from HIV infection, as well as methods of treating an individual suffering from HIV infection.

When taken up by a cell, the genetic constructs of the invention may remain present in the cell as a functioning extrachromosomal molecule and/or integrate into the cell's chromosomal DNA. DNA may be introduced into cells where it remains as separate genetic material in the form of a plasmid or plasmids. Alternatively, linear DNA which can integrate into the chromosome maybe introduced into the cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the genetic constructs of the invention as a linear minichromosome including a centromere, telomeres and an origin of replication.

Genetic constructs of the invention include regulatory elements necessary for gene expression of a nucleic acid molecule. The elements include: a promoter, an initiation codon, a stop codon, and a polyadenylation signal. In addition, enhancers are often required for gene expression of the sequence that encodes the protein of the invention. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to human and bovine growth hormone polyadenylation signals, SV40 polyadenylation signals and LTR polyadenylation signals. In particular, the SV40 polyadenylation signal which is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs of the invention can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments related to immunization applications, nucleic acid molecule(s) are delivered which include nucleotide sequences that encode HIV VVN polyproteins, and additionally, genes for proteins which further enhance the immune response against such target proteins. Examples of such genes are those which encode cytokines and lymphokines such as $\alpha$-interferon, gamma-interferon, platelet derived growth factor (PDGF), GC-SF, GM-CSF, TNF, epidermal growth factor (EGF), IL-1, IL-2, IL-4, IL-6, IL-8, IL-10, IL-12 and B7.2. The use of genes for proteins which further enhance the immune response against target proteins are also described in PCT application PCT/US99/04332 filed Feb. 26, 1999 and published as International Publication No. WO 99/43839 on Sep. 2, 1999, which is incorporated herein by reference In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs which are functional in the cells.

The methods of the present invention comprise the step of administering nucleic acid molecules to tissue of the individual. In some preferred embodiments, the nucleic acid molecules are administered intramuscularly, intranasally, intraperatoneally, subcutaneously, intradermally, intravenously, by aerosol administration to lung tissue or topically or by lavage to mucosal tissue selected from the group consisting of vaginal, rectal, urethral, buccal and sublingual.

An aspect of the present invention relates to pharmaceutical compositions useful in the methods of the present invention. The pharmaceutical compositions comprise a nucleic acid molecule, preferably a DNA molecule comprising a nucleotide sequence that encodes one or more proteins operably linked to regulatory elements necessary for expression in the cells of the individual. The pharmaceutical compositions further comprise a pharmaceutically acceptable carrier or diluent. The term "pharmaceutical" is well known and widely understood by those skilled in the art. As used herein, the terms "pharmaceutical compositions" and "injectable pharmaceutical compositions" are meant to have their ordinary meaning as understood by those skilled in the art. Pharmaceutical compositions are required to meet specific standards regarding sterility, pyrogens, particulate matter as well as isotonicity and pH. For example, injectable pharmaceuticals are sterile and pyrogen free.

Pharmaceutical compositions according to the present invention may comprise about 1 ng to about 10,000 µg of DNA. In some preferred embodiments, the pharmaceutical compositions contain about 2000 µg, 3000 µg, 4000 µg or 5000 µg of DNA. In some preferred embodiments, the pharmaceutical compositions contain about 1000 µg of DNA. In some preferred embodiments, the pharmaceutical compositions contain about 10 ng to about 800 µg of DNA. In some preferred embodiments, the pharmaceutical compositions contain about 0.1 to about 500 µg of DNA. In some preferred embodiments, the pharmaceutical compositions contain about 1 to about 350 µg of DNA. In some preferred embodiments, the pharmaceutical compositions contain about 25 to about 250 µg of DNA. In some preferred embodiments, the pharmaceutical compositions contain about 100 µg DNA.

The pharmaceutical compositions according to the present invention which comprise gene constructs of the invention are formulated according to the mode of administration to be used. One having ordinary skill in the art can readily formulate a vaccine or non-immunogenic therapeutic that comprises a genetic construct. In cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. The pharmaceutical preparations according to the present invention are provided sterile and pyrogen free. Pharmaceutical compositions according to the invention include delivery components in combination with nucleic acid molecules which further comprise a pharmaceutically acceptable carriers or vehicles, such as, for example, saline. Any medium may be used which allows for successful delivery of the nucleic acid. One skilled in the art would readily comprehend the multitude of pharmaceutically acceptable media that may be used in the present invention. Suitable pharmaceutical carriers are described in *Remington's Pharmaceutical Sciences*, A. Osol, a standard reference text in this field, which is incorporated herein by reference.

In some embodiments, the nucleic acid molecule is delivered to the cells in conjunction with administration of a facilitating agent. Facilitating agents are also referred to as polynucleotide function enhancers or genetic vaccine facilitator agents. Facilitating agents are described in U.S. Pat. No. 5,830,876 issued Nov. 3, 1998, U.S. Pat. No. 5,593,972 issued Jan. 14, 1997 and International Application Serial Number PCT/US94/00899 filed Jan. 26, 1994 (U.S. Ser. No. 08/979,385 filed Nov. 29, 1997), which are each incorporated herein by reference. In addition, facilitating agents are described in U.S. Pat. No. 5,739,118 issued Apr. 14, 1998, U.S. Pat. No. 5,837,533 issued Nov. 17, 1998, PCT/US95/12502 filed Sep. 28, 1995 and PCT/US95/04071 filed Mar. 30, 1995, which are each incorporated herein by reference. Facilitating agents which are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with or without a facilitating agent include growth factors, cytokines and lymphokines such as α-interferon, gamma-interferon, platelet derived growth factor (PDGF), GC-SF, GM-CSF, TNF, epidermal growth factor (EGF), IL-1, IL-2, IL-4, IL-6, IL-8, IL-10, IL-12 and B7.2 as well as fibroblast growth factor, surface active agents such as immune-stimulating complexes (ISCOMS), Freund's incomplete adjuvant, LPS analog including monophosphoryl Lipid A (MPL), muramyl peptides, quinone analogs and vesicles such as squalene and squalene, and hyaluronic acid. In embodiments which relate to methods of immunizing, co-agents are selected which preferably enhance immune responses. In embodiments which relate to methods of immunosuppressing, co-agents are selected which do not enhance immune responses.

In some preferred embodiments, the genetic constructs of the invention are formulated with or administered in conjunction with a facilitator selected from the group consisting of benzoic acid esters, anilides, amidines, urethans and the hydrochloride salts thereof such as those of the family of local anesthetics.

The facilitators in some preferred embodiments may be a compound having one of the following formulae:

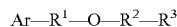

or

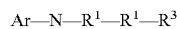

or

or

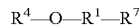

wherein:
Ar is benzene, p-aminobenzene, m-aminobenzene, o-aminobenzene, substituted benzene, substituted p-aminobenzene, substituted m-aminobenzene, substituted o-aminobenzene, wherein the amino group in the aminobenzene compounds can be amino, $C_1$-$C_5$ alkylamine, $C_1$-$C_5$, $C_1$-$C_5$ dialkylamine and substitutions in substituted compounds are halogen, $C_1$-$C_5$ alkyl and $C_1$-$C_5$ alkoxy;
$R^1$ is C=O;
$R^2$ is $C_1$-$C_{10}$ alkyl including branched alkyls;
$R^3$ is hydrogen, amine, $C_1$-$C_5$ alkylamine, $C_1$-$C_5$, $C_1$-$C_5$ dialkylamine;
$R^2$+$R^3$ can form a cyclic alkyl, a $C_1$-$C_{10}$ alkyl substituted cyclic alkyl, a cyclic aliphatic amine, a $C_1$-$C_{10}$ alkyl substituted cyclic aliphatic amine, a heterocycle, a $C_1$-$C_{10}$ alkyl substituted heterocycle including a $C_1$-$C_{10}$ alkyl N-substituted heterocycle;
$R^4$ is Ar, $R^2$ or $C_1$-$C_5$ alkoxy, a cyclic alkyl, a $C_1$-$C_{10}$ alkyl substituted cyclic alkyl, a cyclic aliphatic amine, a $C_1$-$C_{10}$ alkyl substituted cyclic aliphatic amine, a heterocycle, a $C_1$-$C_{10}$ alkyl substituted heterocycle and a $C_1$-$C_{10}$ alkoxy substituted heterocycle including a $C_1$-$C_{10}$ alkyl N-substituted heterocycle;
$R^5$ is C=NH;
$R^6$ is Ar, $R^2$ or $C_1$-$C_5$ alkoxy, a cyclic alkyl, a $C_1$-$C_{10}$ alkyl substituted cyclic alkyl, a cyclic aliphatic amine, a $C_1$-$C_{10}$ alkyl substituted cyclic aliphatic amine, a heterocycle, a $C_1$-$C_{10}$ allyl substituted heterocycle and a $C_1$-$C_{10}$ alkoxy substituted heterocycle including a $C_1$-$C_{10}$ alkyl N-substituted heterocycle; and.
$R^7$ is Ar, $R^2$ or $C_1$-$C_5$ alkoxy, a cyclic alkyl, a $C_1$-$C_{10}$ alkyl substituted cyclic alkyl, a cyclic aliphatic amine, a $C_1$-$C_{10}$ alkyl substituted cyclic aliphatic amine, a heterocycle, a $C_1$-$C_{10}$ alkyl substituted heterocycle and a $C_1$-$C_{10}$ alkoxy substituted heterocycle including a $C_1$-$C_{10}$ alkyl N-substituted heterocycle.

Examples of esters include: benzoic acid esters such as piperocaine, meprylcaine and isobucaine; para-aminobenzoic acid esters such as procaine, tetracaine, butethamine, propoxycaine and chloroprocaine; meta-aminobenzoic acid esters including metabuthamine and primacaine; and para-ethoxybenzoic acid esters such as parethoxycaine. Examples of anilides include lidocaine, etidocaine, mepivacaine, bupivacaine, pyrrocaine and prilocalne. Other examples of such compounds include dibucaine, benzocaine, dyclonine, pramoxine, proparacaine, butacaine, benoxinate, carbocaine, methyl bupivacaine, butasin picrate, phenacaine, diothan, luccaine, intracaine, nupercaine, metabutoxycaine, piridocaine, biphenamine and the botanically-derived bicyclics such as cocaine, cinnamoylcocaine, truxilline and cocaethylene and all such compounds complexed with hydrochloride.

In preferred embodiments, the facilitator is bupivacaine. The difference between bupivacaine and mepivacaine is that bupivacaine has a N-butyl group in place of an N-methyl group of mepivacaine. Compounds may have at that N, $C_1$-$C_{10}$. Compounds may be substituted by halogen such as procaine and chloroprocaine. The anilides are preferred.

The facilitating agent is administered prior to, simultaneously with or subsequent to the genetic construct. The facilitating agent and the genetic construct may be formulated in the same composition.

Bupivacaine-HCl is chemically designated as 2-piperidinecarboxamide, 1-butyl-N-(2,6-dimethylphenyl)-monohydrochloride, monohydrate and is widely available commercially for pharmaceutical uses from many sources including from Astra Pharmaceutical Products Inc. (Westboro, Mass.) and Sanofi Winthrop Pharmaceuticals (New York, N.Y.), Eastman Kodak Rochester, N.Y.). Bupivacaine is commercially formulated with and without methylparaben and with or without epinephrine. Any such formulation may be used. It is commercially available for pharmaceutical use in concentration of 0.25%, 0.5% and 0.75% which may be used on the invention. Alternative concentrations, particularly those between 0.05%-1.0% which elicit desirable effects may be prepared if desired. According to the present invention, about 250 µg to about 10 mg of bupivacaine is administered. In some embodiments, about 250 µg to about 7.5 mg is administered. In some embodiments, about 0.05 mg to about 5.0 mg is administered. In some embodiments, about 0.5 mg to about 3.0 mg is administered. In some embodiments about 5 to 50 µg is administered. For example, in some embodiments about 50 µl to about 2 ml, preferably 50 µl to about 1500 µl and more preferably about 1 ml of 0.25-0.50% bupivacaine-HCl and 0.1% methylparaben in an isotonic pharmaceutical carrier is administered at the same site as the vaccine before, simultaneously with or after the vaccine is administered. Similarly, in some embodiments, about 50 µl to about 2 ml, preferably 50 µl to about 1500 µl and more preferably about 1 ml of 0.25-0.50% bupivacaine-HCl in an isotonic pharmaceutical carrier is administered at the same site as the vaccine before, simultaneously with or after the vaccine is administered. Bupivacaine and any other similarly acting compounds, particularly those of the related family of local anesthetics may be administered at concentrations which provide the desired facilitation of uptake of genetic constructs by cells.

In some embodiments of the invention, the individual is first subject to injection of the facilitator prior to administration of the genetic construct. That is, up to, for example, up to a about a week to ten days prior to administration of the genetic construct, the individual is first injected with the facilitator. In some embodiments, the individual is injected with facilitator about 1 to 5 days, in some embodiments 24 hours, before or after administration of the genetic construct. Alternatively, if used at all, the facilitator is administered simultaneously, minutes before or after administration of the genetic construct. Accordingly, the facilitator and the genetic construct may be combined to form a single pharmaceutical compositions.

In some embodiments, the genetic constructs are administered free of facilitating agents, that is in formulations free from facilitating agents using administration protocols in which the genetic constructions are not administered in conjunction with the administration of facilitating agents.

In some embodiments relating to immunization, gene constructs of the invention may remain part of the genetic material in attenuated live microorganisms or recombinant microbial vectors. The present invention relates to improved attenuated live vaccines and improved vaccines which use recombinant vectors to deliver the VVN polyproteins and/or nucleic acid molecules that encode the polyproteins. Examples of attenuated live vaccines and those using recombinant vectors to deliver foreign antigens are described in U.S. Pat. Nos. 4,722,848; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; and 5,482,713, which are each incorporated herein by reference. Gene constructs are provided which include the nucleotide sequence that encodes an HIV VVN polyprotein is operably linked to regulatory sequences that can function in the vaccinee to effect expression. The gene constructs are incorporated in the attenuated live vaccines and recombinant vaccines to produce improved vaccines according to the invention. Gene constructs may be part of genomes of recombinant viral vaccines where the genetic material either integrates into the chromosome of the cell or remains extrachromosomal.

Some embodiments of the invention relate to proteins and methods of using the same. For example, in some methods of immunizing, HIV VVN polyprotein is administered to individuals. As used herein, the term "proteins of the invention" is intended to mean HIV VVN polyprotein which each can be produced by similar means and which can be formulated and administered in a similar manner for use in methods of the invention.

Vectors including recombinant expression vectors that comprises a nucleotide sequence that encodes proteins of the invention can be produced routinely. As used herein, the term "recombinant expression vector" is meant to refer to a plasmid, phage, viral particle or other vector which, when introduced into an appropriate host, contains the necessary genetic elements to direct expression of a coding sequence. One having ordinary skill in the art can isolate or synthesize a nucleic acid molecule that encodes a protein of the invention and insert it into an expression vector using standard techniques and readily available starting materials. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. Some embodiments of the invention relate to recombinant expression vectors comprises a nucleotide sequence that encodes an HIV VVN polyprotein. The recombinant expression vectors of the invention are useful for transforming hosts. The present invention relates to a recombinant expression vectors that comprises a nucleotide sequence that encodes an HIV VVN polyprotein.

The present invention relates to a host cell that comprises the recombinant expression vector that includes a nucleotide sequence that encodes an HIV VVN polyprotein. Host cells for use in well known recombinant expression systems for production of proteins are well known and readily available. Examples of host cells include bacteria cells such as *E. coli*, yeast cells such as *S. cerevisiae*, insect cells such as *S. frugiperda*, non-human mammalian tissue culture cells chinese hamster ovary (CHO) cells and human tissue culture cells such as HeLa cells.

In some embodiments, for example, one having ordinary skill in the art can, using well known techniques, insert DNA molecules into a commercially available expression vector for use in well known expression systems. For example, the commercially available plasmid pSE420 (Invitrogen, San Diego, Calif.) may be used for production of a CD80ΔC mutant protein in *E. coli*. The commercially available plasmid pYES2 (Invitrogen, San Diego, Calif.) may, for example, be used for production in *S. cerevisiae* strains of yeast. The commercially available MABAC™ complete baculovirus expression system (Invitrogen, San Diego, Calif.) may, for example, be used for production in insect cells. The commercially available plasmid pcDNA I or pcDNA3 (Invitrogen, San Diego, Calif.) may, for example, be used for production in mammalian cells such as Chinese Hamster Ovary cells. One having ordinary skill in the art can use these commercial expression vectors and systems or others to produce proteins of the invention using routine techniques and readily available starting materials. (See e.g., Sambrook et al., *Molecular Cloning a Laboratory Manual*, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989).

The expression vector including the DNA that encodes a protein of the invention is used to transform the compatible host which is then cultured and maintained under conditions wherein expression of the foreign DNA takes place. The protein of the invention thus produced is recovered from the culture, either by lysing the cells or from the culture medium as appropriate and known to those in the art. One having ordinary skill in the art can, using well known techniques, isolate the protein of the invention that is produced using such expression systems. The methods of purifying proteins of the invention from natural sources using antibodies which specifically bind to such protein are routine as is the methods of generating such antibodies (See: Harlow, E. and Lane, E., *Antibodies: A Laboratory Manual*, 1988, Cold Spring Harbor Laboratory Press which is incorporated herein by reference.). Such antibodies may be used to purifying proteins produced by recombinant DNA methodology or natural sources.

Examples of genetic constructs include coding sequences which encode a protein of the invention and which are operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes proteins of the invention from readily available starting materials. Such gene constructs are useful for the production of proteins of the invention.

In addition to producing proteins of the invention by recombinant techniques, automated peptide synthesizers may also be employed to produce proteins of the invention. Such techniques are well known to those having ordinary skill in the art and are useful if derivatives which have substitutions not provided for in DNA-encoded protein production.

The proteins of the invention may be prepared by any of the following known techniques. Conveniently, the proteins of the invention may be prepared using the solid-phase synthetic technique initially described by Merrifield, in *J. Am. Chem. Soc.*, 15:2149-2154 (1963) which is incorporated herein by reference. Other protein synthesis techniques may be found, for example, in M. Bodanszky et al., (1976) *Peptide Synthe-sis*, John Wiley & Sons, 2d Ed. which is incorporated herein by reference; Kent and Clark-Lewis in *Synthetic Peptides in Biology and Medicine*, p. 295-358, eds. Alitalo, K., et al. Science Publishers, (Amsterdam, 1985) which is incorporated herein by reference; as well as other reference works known to those skilled in the art. A summary of synthesis techniques may be found in J. Stuart and J. D. Young, *Solid Phase Peptide Synthelia*, Pierce Chemical Company, Rockford, Ill. (1984) which is incorporated herein by reference. Synthesis by solution methods may also be used, as described in *The Proteins*, Vol. 1, 3d Ed., p. 105-237, Neurath, H. et al., Eds., Academic Press, New York, N.Y. (1976) which is incorporated herein by reference. Appropriate protective groups for use in such syntheses will be found in the above texts, as well as in J. F. W. McOmie, *Protective Groups in Organic Chemistry*, Plenum Press, New York, N.Y. (1973) which is incorporated herein by reference.

In general, these synthetic methods involve the sequential addition of one or more amino acid residues or suitable protected amino acid residues to a growing peptide chain. Normally, either the amino or carboxyl group of the first amino acid residue is protected by a suitable, selectively-removable protecting group. A different, selectively removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

In some embodiments, proteins may be produced in transgenic animals. The present invention relates to a transgenic non-human mammal that comprises the recombinant expression vector that comprises a nucleic acid sequence that encodes an HWV VVN polyprotein. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes an HIV VVN polyprotein is operably linked to a mammary cell specific promoter whereby the coding sequence is only expressed in mammary cells and the recombinant protein so expressed is recovered from the animal's milk. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce an HI VVN polyprotein. Preferred animals are goats, and rodents, particularly rats and mice.

Conservative substitutions of amino acid sequences of proteins of the invention are contemplated. As used herein, the term "conservative substitutions" is meant to refer to amino acid substitutions of an HIV VVN polyprotein with other residues which share similar structural and/or charge features. Those having ordinary skill in the art can readily design proteins of the invention with conservative substitutions for amino acids based upon well known conservative groups.

The pharmaceutical compositions of the present invention may be administered by any means that enables the active agent to reach the agent's site of action in the body of a mammal. The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Because peptides are subject to being digested when administered orally, oral formulations are formulated to enterically coat the active agent or otherwise protect it from degradation in the stomach (such as prenuetralization). Parenteral administration includes intravenous drip, subcutaneous, intraperitoneal or intramuscular injection, pulmonary administration, e.g., by inhalation or insufflation, or intrathecal or intraventricular administration. In preferred embodiments, parenteral administration, i.e., intravenous, subcutaneous, transdermal, intramuscular, is ordinarily used to optimize absorption. Intravenous administration may be accomplished with the aid of an infusion pump. The pharmaceutical compositions of the present invention may be formulated as an emulsion.

One skilled in the art would readily comprehend the multitude of pharmaceutically acceptable media that maybe used in the present invention. Suitable pharmaceutical carriers are described in *Remington's Pharmaceutical Sciences*, A. Osol, a standard reference text in this field, which is incorporated herein by reference. Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Compositions for oral administration include powders or granules, suspensions or solutions in water or non-aqueous media, capsules, sachets or tablets. Thickeners, flavoring agents, diluents, emulsifiers, dispersing aids or binders may be desirable. Compositions for parenteral, intravenous, intrathecal or intraventricular administration may include sterile aqueous solutions which may also contain buffers, diluents and other suitable additives and are preferably sterile and pyrogen free. Pharmaceutical compositions which are suitable for intravenous administration according to the invention are sterile and pyrogen free. For parenteral administration, the peptides of the invention can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution The pharmaceutical compositions according to the present invention may be administered as a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Formulation of therapeutic compositions and their subsequent administration is believed to be within the skill of those in the art. Usually, the dosage of peptide can be about 1 to 3000 milligrams per 50 kilograms of body weight; preferably 10 to 1000 milligrams per 50 kilograms of body weight; more preferably 25 to 800 milligrams per 50 kilograms of body weight. Ordinarily 8 to 800 milligrams are administered to an individual per day in divided doses 1 to 6 times a day or in sustained release form is effective to obtain desired results.

Depending upon the method for which the protein or proteins are being administered, the pharmaceutical compositions of the present invention may be formulated and administered to most effectively. Modes of administration will be apparent to one skilled in the art in view of the present disclosure.

The methods of the present invention are useful in the fields of both human and veterinary medicine. Accordingly, the present invention relates to genetic immunization of mammals, birds and fish. The methods of the present invention can be particularly useful for mammalian species including human, bovine, ovine, porcine, equine, canine and feline species.

The present invention additionally relates to attenuated human immunodeficiency virus (HIV) accessory proteins Vif, Vpu and Nef, particularly those described and set forth herein, to nucleic acid molecules that encode the same and to vaccines as generally described herein comprising the proteins or nucleic acid and the making and using of the same. In some embodiments, the invention relates to a a single accessory proteins selected from the group consisting of Vif, Vpu and Nef, to nucleic acid molecules that encode the same and to vaccines as generally described herein comprising the single proteins or nucleic acid and the making and using of the same. In some embodiments, the invention relates to a polyprotein comprising two accessory proteins selected from the group consisting of Vif, Vpu and Nef, to nucleic acid molecules that encode the same and to vaccines as generally described herein comprising such polyproteins or nucleic acid and the making and using of the same.

The Examples set out below include representative examples of aspects of the present invention. The Examples are not meant to limit the scope of the invention but rather serve exemplary purposes. In addition, various aspects of the invention can be summarized by the following description. However, this description is not meant to limit the scope of the invention but rather to highlight various aspects of the invention. One having ordinary skill in the art can readily appreciate additional aspects and embodiments of the invention.

EXAMPLE

A DNA vaccine cassette expressing multiple Human Immunodeficiency Virus (HIV-1) accessory genes comprising HIV Vif, HIV Vpu and EEV Nef may be produced as described in Ayyavoo V, (2000), AIDS 14:1-9 which is incorporated herein by reference.

Materials and Methods

Cells: HeLa and NIH3T3 cells, obtained from the American Type Culture Collection (ATCC), were grown in a monolayer at 37° C. in 5% $CO_2$ in Dulbecco's Modified Eagle's medium, 10% fetal bovine serum, 1% penicillin, 1% Streptomycin and 1% L-glutamine. P815 cells obtained from ATCC were maintained as suspension cultures in RPMI 1640, 10% fetal bovine serum, 1% penicillin, 1% Streptomycin and 1% L-glutamine at 37° C. with 5% $CO_2$. Phytohemagglutinin (PHA)-stimulated (5 µg/ml) PBLs were maintained in RPMI 1640 medium containing 10% T-cell growth factor.

Generation of multiple immunogen expression cassettes: HIV-1 vif, vpr, vpu and nef genes were individually cloned using PCR. Attenuated HIV-1 accessory genes vif (N17), vpu (M5256) and nef (S313) were selected to construct the multigene fusion cassettes. To construct the fusion protein and fusion protein with proteolytic cleavage sites, we used the overlap PCR technique. HIV-1 vif, vpu and nef were fused in this order using the following primers:

```
vif(+)  5' ATTGAAAGCTTATGGAAAACAGATGGCAGG 3';                           (SEQ ID NO:5)
vif(-)  5' TACTATTATAGG TTGCATCTCGTGTCCATTCATTGT 3';                    (SEQ ID NO:6)
vpu(+)  5' GGACACGAGATGCAACCTATAATA GTAGCA 3';                          (SEQ ID NO:7)
vpu(-)  5' TGACCACTTGCCACCCATCTCGAGATCATCAATATCCCAAGG 3';               (SEQ ID NO:8)
nef(+)  5' GGAGATGGGTGGCAAGTGGTCAAAAAGT 3'; and                         (SEQ ID NO:9)
nef(-)  5' CGCAAGCTTCG ATGTCAGCAGTCTTTGTAG 3'.                          (SEQ ID NO:10)
```

The same primers were used to construct the fusion protein except the vif (−) primer and vpu (−) primer have an eight amino acid (REKRAVVG) (SEQ ID NO:4) additional proteolytic cleavage sites. The amplified fusion gene products (1.4 kb) were digested with Hind In (sites for which recognition sequences were incorporated into the outer primer pairs), cloned into pcDNA3 (Invitrogen, Calif.), and sequenced to verify mutations and ensure the integrity of the fusion genes.

In Vitro Translation of fusion proteins using T7 system: In vitro transcription and translation was performed on 1 µg of fusion protein expression construct DNA using T7 RNA polymerase according to the mranufacturer's instructions (Promega, Madison, Wis.). Five (5) µl of the in vitro translation reaction products were combined with 500 µl of radio-immunoprecipitation assay buffer and immunoprecipitated with rabbit anti-Vif, anti-Vpu and anti-Nef antisera. The immunoprecipitated products were resolved on 12% SDS-PAGE and autoradiographed.

Western blot (immunoblot analysis): HeLa cells were transfected with 20 µg of pVVN and pVVN-P expression constructs using DOTAP (BMB, IN). Forty-eight hrs following transfection cells were placed in selection medium (DMEM containing 400 µg/ml Geneticin) and single cell clones were isolated. In order to analyze the expression, functionality, and proper cleaving of the proteins by cellular proteases, the stable cells were lysed and the cell lysates were used in immunoprecipitation using anti-Vif, anti-Vpu, and anti-Nef antibodies followed by western blotting.

Immunofluorescence assay: HeLa cells were maintained in DMEM containing 10% FBS and seeded onto poly-L-lysine coated glass coverslips at a density of $1 \times 10^6$ cells per dish (35 mm). Twenty four hours later they were infected with vTF7-3 and transfected as described above. Sixteen to 24 hours after transfection, the cells were washed with PBS and fixed with methanol at room temperature for 30 min. The cells were then washed with PBS and incubated for 90 min. with primary antiserum (1:50). After washing with PBS, the coverslips were incubated for 90 min. with FITC-conjugated affinity purified F(ab)'2 fragment of goat anti-rabbit IgG (ICN Biochemicals; CA) diluted 1:100 in PBS, and washed six times with PBS. Coverslips were then counter stained for 5 min. with DAPI (0.1% in PBS; Sigma; St. Louis, Mo.) and again washed prior to mounting on glass slides using a fade-resistant mounting medium (Citiflour; England). All incubations were carried out at 37° C. in a humidification chamber.

Development of mouse stable cell lines expressing hCD4 and CCR5 or CXCR4 for CTL: NIH3T3 cells were co-transfected with hCD4 expression vector and pBabe-Fusin or hCD4 and pBabe-CCR5 expression vectors using DOTAP (BMB, IN). Forty eight hrs post transfection cells were maintained in 400 µg/ml of Geneticin and 2 µg/ml of puromycin. Stable cell lines were established from single cell clones and analyzed for the expression of hCD4 and Fusin or CCR5 by flow cytometry. Briefly, cells ($5 \times 10^5$) were stained with FITC or PE labeled human mAbs to CD4, CCR5 and Fusin (Pharmingen, Calif.) for 1 hour, washed 2x with FACS buffer (3% BSA, 0.1% $NaN_3$ in 1xPBS), and fixed with 2% paraformaldehyde and analyzed by Fluoresence Activated Cell Sorter (Beckton Dickinson, Calif.).

Virus infection by primary isolates: NIH3T3 cells expressing hCD4/Fusin and hCD4/CCR5 were infected with 10-50 ng of HIV-1 p24 equivalent of primary and well characterized T-tropic (pNL43) and dual tropic (89.6) laboratory isolates. Primary isolates also include viruses derived from different clades C, D, E and A (obtained from WHO through NIH ARRPP). Infectivity of the cells was assayed by measuring the p24 antigen released into the medium. The p24 assay was performed using the p24 capture ELISA kit (Coulter, Fla.) following the manufacturer's instructions.

Mice: Balb/c female mice, aged 6-8 weeks were purchased from Harlan Sprague Dawley, Inc., (Indianapolis, Ind.). The mice were housed in a temperature controlled, light-cycled room as per the guidelines of National Institute of Health and University of Pennsylvania.

DNA inoculation: We have utilized a facilitated DNA inoculation protocol which results in increased protein expression levels from plasmid delivered genes in vivo. Specifically, the quadriceps muscles of BALB/c mice were injected with 100 µl of 0.25% bupivacaine-HCL (Sigma, Mo.) using a 27-gauge needle. Forty eight hours later, 100 µg of DNA construct of interest in phosphate buffer saline was injected into the same region of the muscle as the bupivacaine injection. Mice were given one injection followed by a boost two weeks later. Two weeks after the second injection, half of the mice in each group were sacrificed for their spleens, and the remaining mice were given a second boost with the appropriate DNA construct.

T Helper Cell Proliferation Assay: Lymphocytes from harvested mouse spleens were prepared). The isolated cell suspensions were resuspended to a concentration of $5 \times 10^6$ cells/ml in RPMI 1640 containing 10% FBS. A 100 µl aliquot containing $5 \times 10^5$ cells was added to appropriate well of a 96 well microtiter flat bottom plate as per assay layout. 100 µl of the appropriate protein was added to wells in triplicate at 10 or 2 µg/ml, making the final protein concentration 5 and 1 µg/ml respectively. The cells were incubated at 37° C. in 5% $CO_2$ for three days. One µCi of tritiated thymidine was added to each well and the cells were incubated for 12-18 hrs at 37° C. The plates were harvested and the amount of incorporated tritiated thymidine was measured in a beta plate reader. To ensure that cells were healthy, 10 µg/ml of PHA was used as a polyclonal stimulator positive control. Stimulation Index was determined from the formula: Stimulation Index=(experimental count-spontaneous count)/spontaneous count.

Cytotoxic T Lymphocyte Assay: A 5 hour $^{51}Cr$ release CTL assay was performed using vaccinia infected targets or peptide treated targets. Lymphocytes were harvested from spleens and prepared as the effector cells by removing the erythrocytes and by washing several times with fresh media. The assay was performed both with and without in vitro stimulation of the effectors. In the case of in vitro stimulated assay, the effector cells were stimulated for 1 day with ConcavalinA (Sigma, St. Louis, Mo.) at 2 µg/ml concentration. Effectors were then stimulated for 3 days with relevant vaccinia-infected or 1 µM peptide treated P815cells, which were fixed with 0.1% glutaraldehyde and 0.1M Glycine. Vaccinia infected targets were prepared by infecting $3 \times 10^6$ P815 cells for 5-12 hours at 37° C. Peptide pulsed targets were prepared by incubating P815 cells for 5-12 hours with peptides. The target cells were labeled with 100 µCi/ml $Na_2^{51}CrO_4$ for 60-120 min. and then incubated with the stimulated spleenocytes for 4-6 hours at 37° C. CTL was tested at effector:target (E:T) ratios ranging from 50:1 to 12.5:1. Supernatants were harvested and counted on a LKB Gamma-counter. Percent specific lysis was determined from the formula: 100×{(experimental release−spontaneous release)/(maximum release−spontaneous release)}. Maximum release was determined by lysis of target cells in 5% Triton X-100 containing medium. Recombinant vaccinia (vNef and vSC8) were obtained from the NIH AIDS Research and Reference Reagent Program.

CTL using clinical HIV-1 isolates infected targets: NIH3T3 cells expressing hCD4/Fusin or hCD4/CCR5 were infected with HIV-1 laboratory and clinical isolates representing both T-tropic and MO-tropic viruses. HIV-1 infected NIH3T3 clones were labeled with chromium and used as targets in CTL assay.

Cross Clade CTL Killing: HIV-1 viruses isolated from different clades were used to infect NIH3T3 cells expressing hCD4/Fusin and hCD4/CCR5. Infectivity was assayed by measuring p24 antigen and infected cells were used as targets in the CTL assay.

Results

Construction and characterization of attenuated vif, vpu and nef genes for DNA immunization: HIV-1 accessory genes vif, vpu and nef were cloned from HIV-1 positive patients and analyzed for their function and attenuated. Biological characterization of these genes was performed following the standard functional assays as seen in Table 1. Attenuated vif, vpu and nef clones were selected for further immunological analyses in mice. Functional (wild type) and a number of non-functional (attenuated) vif, vpi; vpu and nef clones were used to immunize mice and the immune responses generated were measured. Groups of mice were immunized with one of the vaccine constructs and given an additional boost 15 days later. Animals were subsequently sacrificed two weeks after the second injection and their spleens were obtained for use in a cytotoxic T cell (CTL) and lymphoproliferative assays. Due to availability of reagents for CTL, P815 cells expressing Vif or P815 infected with Nef expressing vaccinia were used as target cells. Both functional and attenuated vif and nef constructs are capable of inducing antigen specific CTL compared to vector construct immunized mice.

FIG. 1A shows the percentage of specific CTL activity induced by both functional and attenuated vif and nef constructs. 100 µg of wild type and attenuated nef or vif expression plasmid was administered intramuscularly in mice. Two weeks after the first injection, the mice were boosted once with the same dosage of the respective plasmid. After 2 additional weeks, the CTL assay was performed on spleen cells harvested from immunized mice as described in methods. The assay was conducted on the day of spleen harvest measuring the chromium release from specific and irrelevant vaccinia infected targets. The control group immunized with only vector backbone resulted in no specific lysis of target cells above the background level. Vaccinia expressing β-gal (vSC8) was used to infect p815 to prepare irrelevant targets. Similar results were obtained in multiple experiments. At a 50:1 effector: target ratio, vif clones T-37 (functional) and N-17 (attenuated) exhibited 19.9 and 25% specific lysis respectively. These results demonstrate that DNA immunization by different vif constructs induces antigen specific CTL responses. Similarly the functional nef clone (Nef-Mn) and an attenuated nef clone (Nef-Hxb2) are capable of inducing specific cytotoxic T cell lysis against Nef vaccinia infected targets.

Figure 1B:
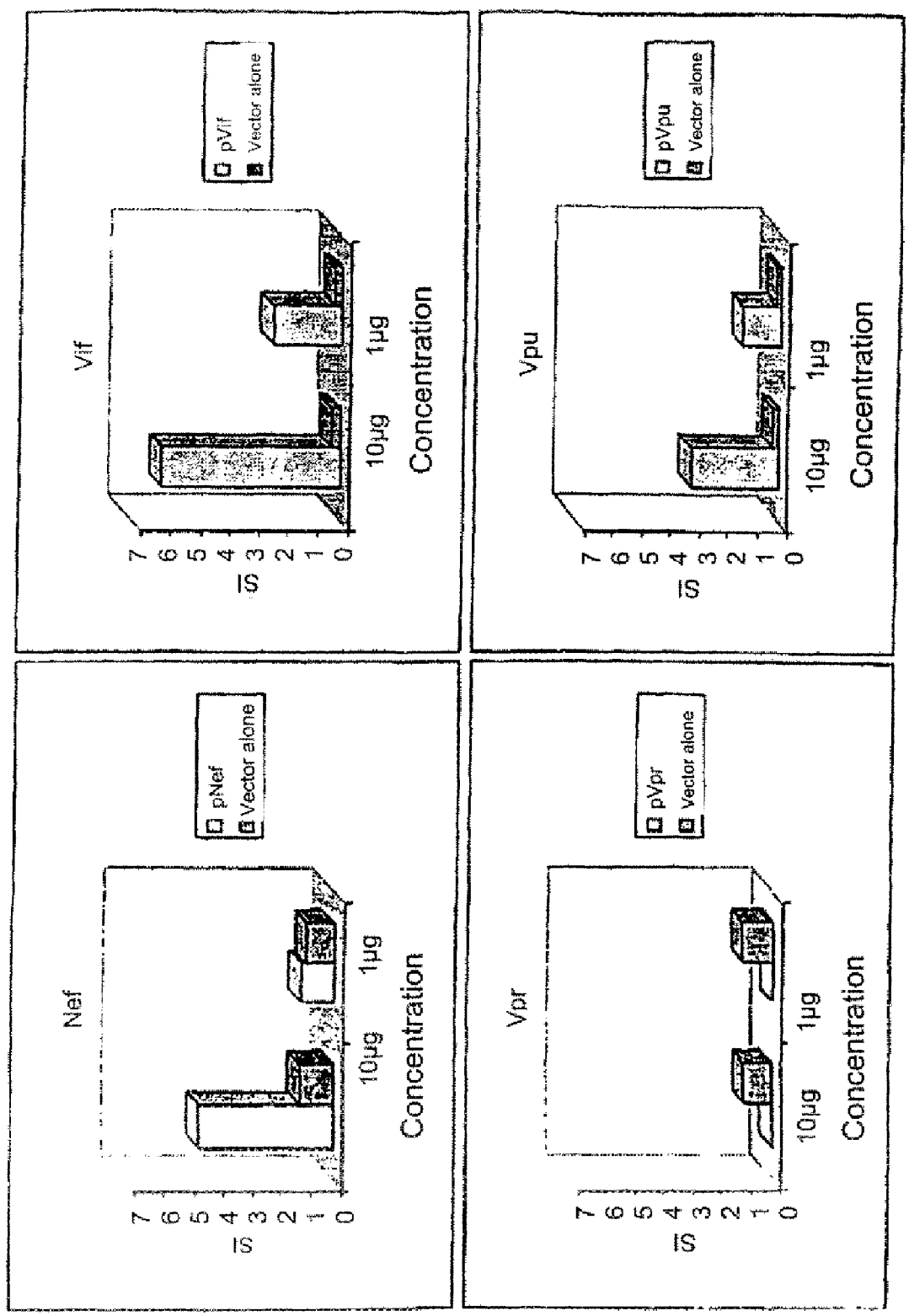

We have also measured the T cell proliferative responses induced by the attenuated vif, vpr, vpu and nef clones with their respective antigen stimulation. FIG. 1B shows data from T cell proliferation experiments in which T cell proliferation was induced by immunization of plasmids expressing vif vpu, vpr and nef 100 µg of respective cDNA expression cassettes were injected intramuscularly in mice and the mice were boosted once after 2 weeks. After one week following the boost, spleenocytes were isolated from 2 mice and pooled and used for T cell proliferation. Spleenocytes were stimulated with 5 and 1 µg/ml recombinant protein for 3 days. One µCi $^3H$ was added and the incorporated cpm was counted. PHA was added as a positive control. Antigen specific stimulation (SI) was calculated and presented for Vif, Vpu and Nef. Similar results were obtained at least in three separate experiments. Results indicate that vif, vpu and nef are capable of inducing a significant lymphoproliferative response, whereas stimulation by Vpr antigen was of no benefit in this assay. Based on these results and the information available from earlier studies, the accessory gene vpr is not included in the present study as part of the multigene vaccine construct.

Our results indicate that pathogenic genes can be used as immunogens after identifying the functional domains and attenuating the domains with out interfering with the expression of the antigen. For further construction of a multigene cassette, we have used the attenuated vif, vpu and nef clones.

Figure 2A:
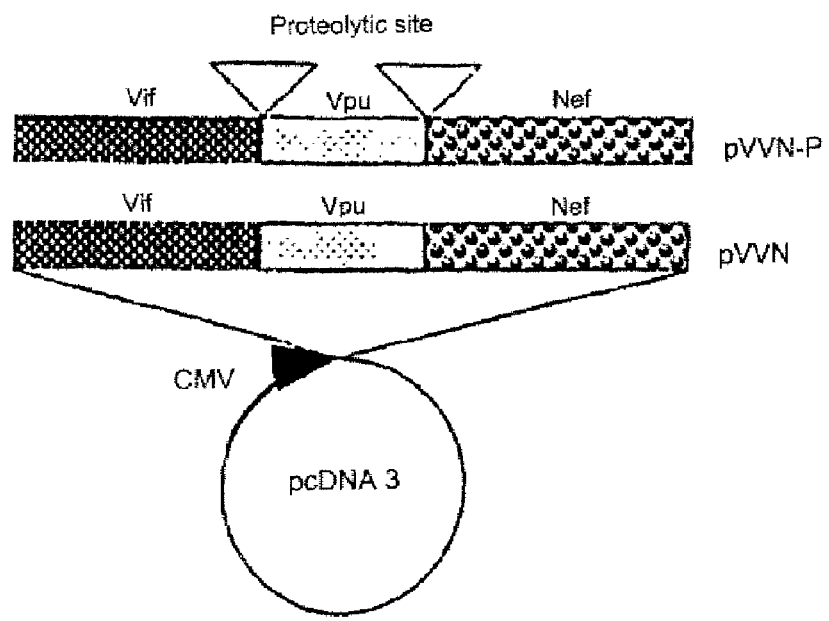
FIG. 2A depicts constructs and FIG. 2B shows data from experiments described in the Example.

Construction and expression of vif/vpu/nef fusion protein cassette (pVVN) and vif/vpu/nef fusion protein construct with proteolytic cleavage sites (pVVN-P): In order to construct a multigene DNA expression cassette containing the accessory genes as fusion protein, we selected the attenuated yet immunologically active vif (N17) vpu (M5256) and nef (S313) clones as the foundation. The stop codon of vif and vpu were removed and fused in frame so that the fusion protein will have the same epitopes as the individual genes. This vif/vpu/nef fusion gene construct is referred to as pVVN. We also wished to conserve the natural amino and carboxy termini by expressing vfi/vpu/nef fusion protein with proteolytic cleavage sites, which is referred here as pVVN-P. FIG. 2A depicts the construction and design of vif, vpu and nef fusion protein and fusion protein with proteolytic cleavage sites as single expression cassettes. Stop codon of vif and vpu were deleted and the following sequences were fused in frame. pVVN represents the expression of vif, vpu and nef as a single gene; pVVN-P represents the expression of vif, vpu and nef as a single gene with proteolytic cleavage site between vif and vpu and vpu and nef: In the pVVN-P fusion protein, the stop codon of vif and vpu were removed and an eight amino acid cellular proteolytic cleavage site (REKRAVVG) was placed in frame to allow cleavage from the following protein sequence.

Figure 2B:
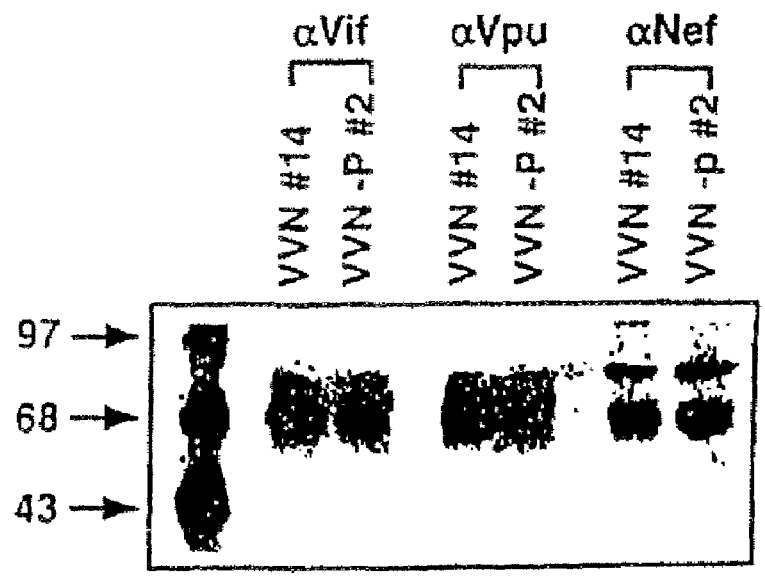

To test whether the new fusion constructs were functional in producing the fusion gene protein(s) an in vitro translation was performed on both pVVN and pVVN-p followed by immunoprecipitation with specific antibodies to Vif, Vpu, and Nef. By themselves, Vif, Vpu and Nef express as 24, 10 and 27 kDa proteins, respectively. In vitro translation of pVVN and pVVN-P vectors resulted in the expression of a 61 kDa fusion protein as expected that was detectable with antibodies specific for the three proteins. FIG. 2B shows data from the expression of VVN and VVN-P following in vitro translation using T7 system. One µg of pVVN (clone #14) and pVVN-P (clone #2) DNA was used in the in vitro translation system. In vitro translated products were immunoprecipitated with anti-Vif (aVif), anti-Vpu (aVpu) and anti-Nef (aNef) antibodies.

Figure 3A:
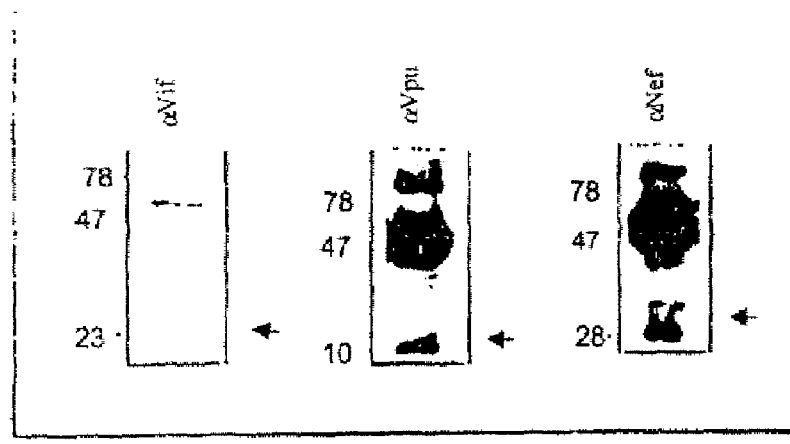
FIGS. 3A, 3B and 3C show data from experiments described in the Example.

Expression and sub cellular localization of VVN and VVN-P fusion proteins in HeLa cells: Expression of VVN and VVN-P fusion proteins in mammalian cells was assessed using the HeLa-VVN and HeLa-VVN-P stable cell lines expressing pVVN and pVVN-P constructs, respectively. After transfection with the DNA vectors, cells were grown in selection medium for two days, washed twice with PBS, and lysed. Cell lysate was incubated with anti-vif, anti-vpu and anti-nef antibodies, immunoprecipitated and resolved on a SDS-PAGE gel, and subjected to immunoblot analysis. Transfection of pVVN in HeLa cells resulted in the expression of a 61 kDa fusion protein, which was detected by all three antibodies (data not shown). In contrast, pVVN-P transfection resulted in both a higher molecular weight species as well as 24, 10 and 27 kDa proteins recognized by anti-Vif, anti-Vpu and anti-Nef antibodies respectively. FIG. 3A shows data related to the expression and processing of VVN and VVN-P fusion protein in HeLa cells by immunoprecipitaion. HeLa cells were transfected with pVVN-P plasmids for overnight. Cells were maintained for 48 hrs in normal before place them in G418 selection. G418 selection was carried out for 2 weeks and the cells were lysed and immunoprecipitated with anti-Vif, anti-Vpu and anti-Nef antibodies as described in materials and methods. Immumoprecipitates were analyzed by SDS-PAGE (12%). Designations of the anti sera are indicated at the top and the cleaved products are marked with an arrow. The results indicate that in vivo expression of pVVN results in a fusion protein and in vivo expression of pVVN-P results in the fusion protein being cleaved at least partially by the cellular proteases as expected.

Figure 3B:
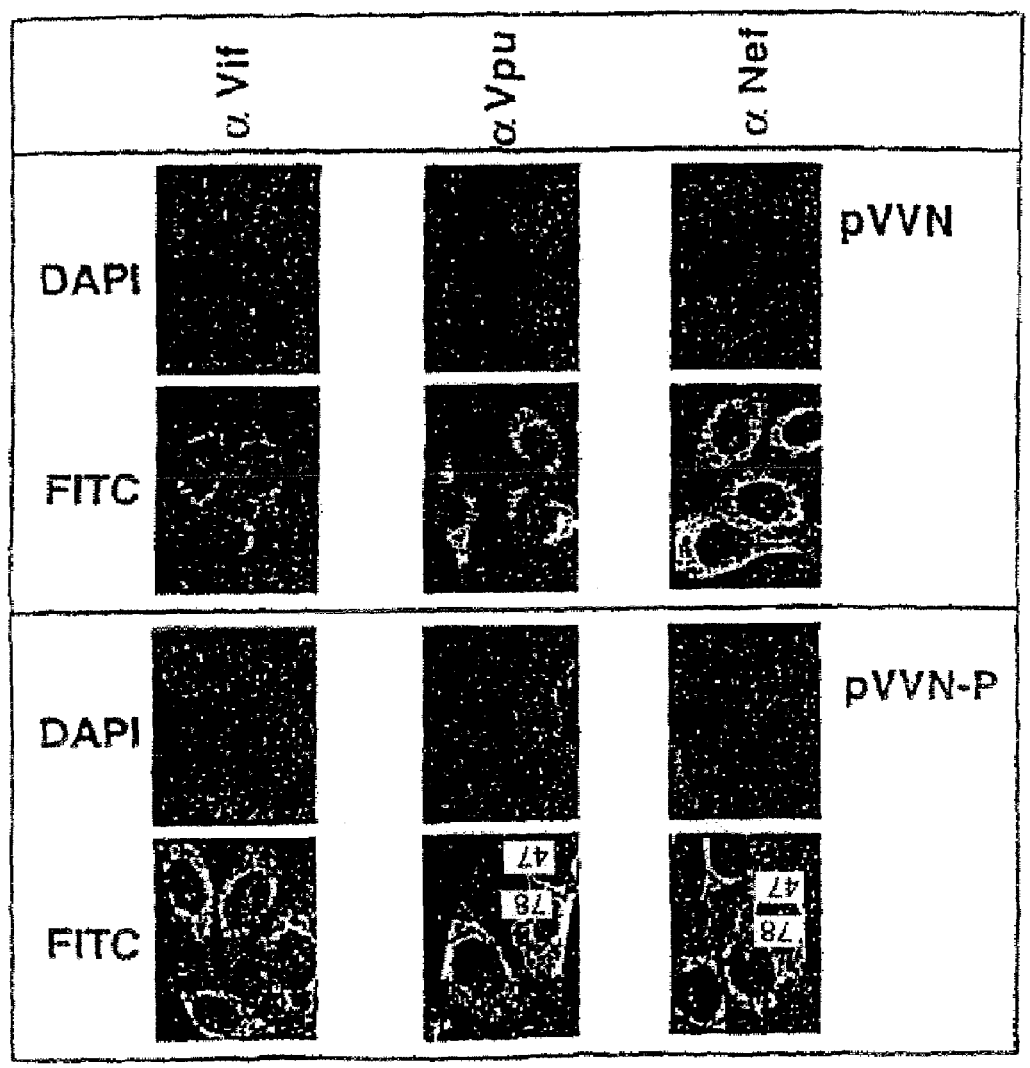
Figure 3C:
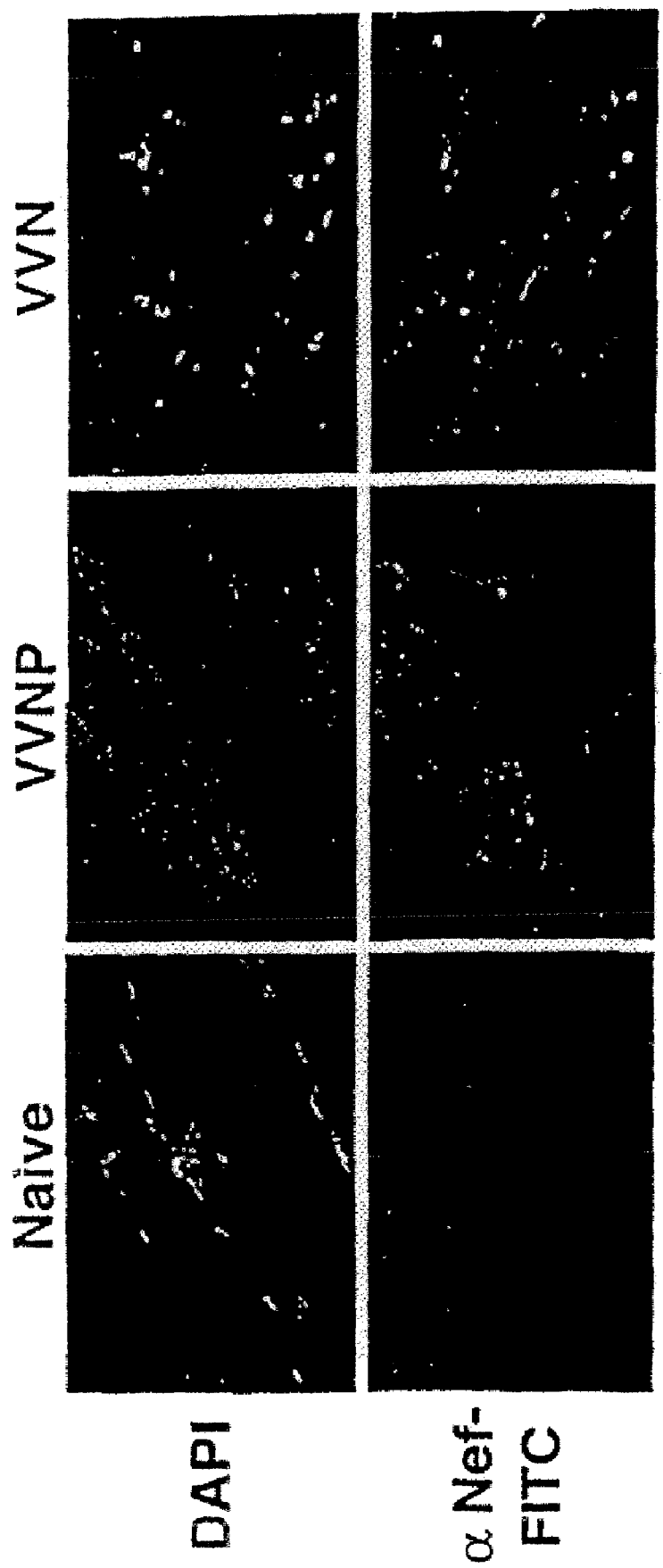

In HIV-1 infected cells, Vif, Vpu and Nef are normally present in the cytoplasmic membranes. In order to verify whether fusing these proteins into a single protein or into a fusion protein with proteolytic cleavage sites changes their cellular localization, we performed immunofluoresence and immunohistochemical studies in vitro and in vivo. HeLa cells were transfected with pVVN and pVVN-P and localization of the vif/vpu/nef fusion protein and fusion protein with proteolytic sites was studied by indirect immunofluoresence using anti-Vif, anti-Vpu and anti-Nef antibodies. FIG. 3B shows data related to the subcellular localization of VVN and VVN-P fusion proteins in vivo. HeLa cells were infected with recombinant vaccinia virus vTF7-3 and transfected with VVN and VVN-P expression plasmids. After overnight transfection, the cells were fixed and stained with anti-Vif, anti-Vpu and anti-Nef sera followed by affinity-purified fluorescein isothiocynate-conjugated goat anti-rabbit immunoglobulin G. Since all the anti sera were raised in rabbit they couldn't be combined in a single immunoflouresence. DAPI, nuclear staining; FITC, represent specific anti serum stained cells. The data in FIG. 3B shows that Vif, Vpu and Nef maintain their wild type cytoplasmic localization pattern either as a fusion protein or fusion protein with proteolytic sites. The results indicate that fusing these genes did not alter their sub cellular distribution pattern, and suggests that both gene products are subjected to the same processing pathway as that of wild type genes and therefore could be presented to the MHC molecules similar to wild type. Additionally, we have also analyzed the expression of VVN and VVN-P iii vivo by performing immunohistochemical analysis on muscle sections of mice immunized with pVVN and pVVN-P, using anti-Nef antibodies. Immunohistochemistry of muscle sections indicated that both VVN and VVN-P fusion proteins could be expressed to high levels in vivo through gene delivery. FIG. 3C shows results of immunohistochemical analysis of VVN and VVN-P antigen expression. Frozen muscle sections from naive, pVVN and pVVN-P immunized mice were prepared five days post immunization and stained with anti-Nef antibodies. Panel (DAPI) represents the nuclear staining and panel (FITC) represents specific staining with anti-Nef antibodies. The positive cells are stained with FITC. Five panels were examined for each staining for each experiment.

T Helper Cell Proliferation Assay: Activation and proliferation of T helper lymphocytes play a critical role in inducing both humoral immune response by signaling for the expansion of antigen-activated B cells and cellular immune response producing cellular signals for the expansion of $CD8^+$ cytotoxic T lymphocytes. Groups of mice (four per group) were injected with one of the two constructs or vector alone. Two weeks after the first DNA immunization, the mice were boosted with same dosage. After 2 additional weeks, spleens were collected from immunized mice and their lymphocytes were isolated. These cells were then tested for T cell proliferation as described in methods. FIG. 4 shows data from experiments described relating to T cell proliferation of spleenocytes from mice immunized with pVVN and pVVN-P following recombinant Vif, Vpu and Nef in vitro stimulation. 100 µg of respective cDNA expression cassettes were injected intramuscularly in mice and the mice were boosted once after 2 weeks. After one week following the boost, spleenocytes were isolated from 2 mice and pooled and used for T cell proliferation. Spleenocytes were stimulated with 5 and 1 µg/ml recombinant protein for 3 days. One µCi $^3$H was added the incorporated cpm was counted. PHA was added as a positive control. DNA constructs used are designated at the bottom. Antigen specific stimulation (SI) was calculated and presented for Vif, Vpu and Nef. Similar results were obtained in multiple experiments. FIGS. 4A, 4B and 4C show the proliferation assay results for the mice immunized with DNA vaccine cassettes pVVN and pVVN-P using Vif, Vpu and Nef proteins as antigens. Recombinant proteins (10 µg/ml) were plated in each well to stimulate proliferation of T cells. 10 µg/ml of the lectin (PHA) was used as a polyclonal stimulator positive control. As shown, a low background level of proliferation (stimulation index of 0.2 to 1) was observed in the control group of naive mouse spleens. A moderate level of proliferation against all the three proteins was observed in spleenocytes from the groups immunized with pVVN and pVVN-P (FIGS. 4A, 4B and 4C). In order to confirm that VVN and VVN-P induce comparable T cell proliferation, we performed T cell proliferation with mice immunized with single gene constructs also in parallel. Vif by it self, or in VVN and VVN-P fusion proteins resulted in SI of 6, 5 and 5.4 respectively (FIG. 4A). Similar results were obtained using Vpu protein (FIG. 4B) and recombinant Nef protein (FIG. 4C) as antigens.

Figure 5:
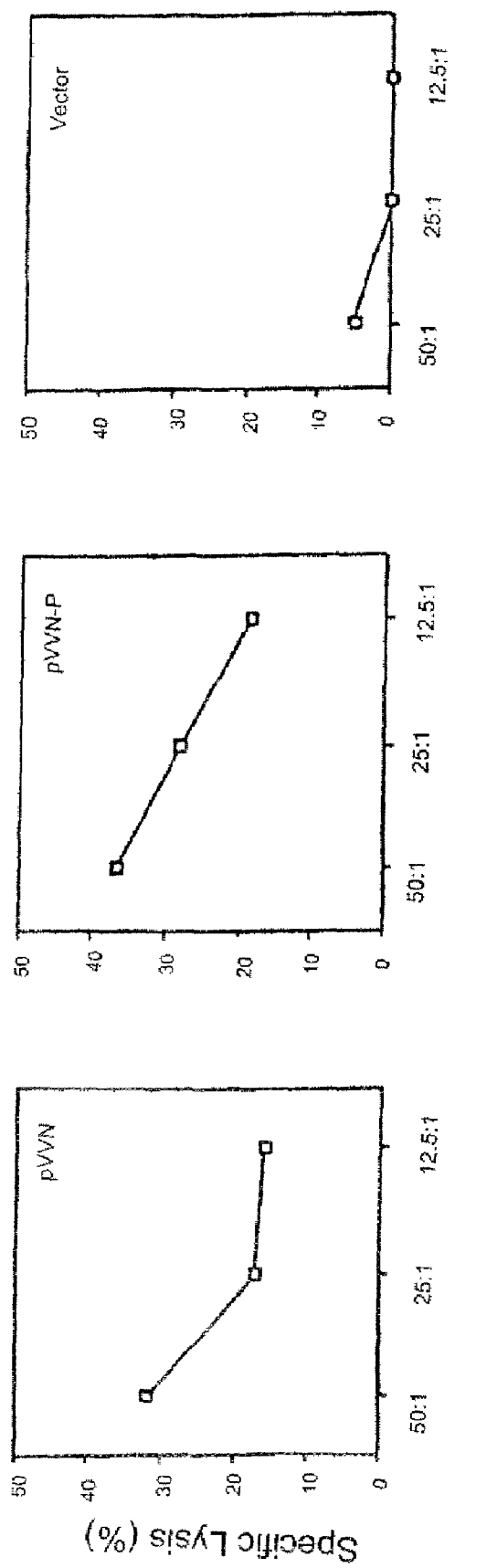
FIG. 5 shows data from experiments described in the Example relating to cytotoxic T lymphocyte response induced by pVVN and pVVN-P immunization.

Cytotoxic T Lymphocyte activity using Nef vaccinia: To further investigate the induction of the resultant cellular immune response by these constructs, we conducted cytotoxic T lymphocyte (CTL) assays on spleenocytes of mice immunized with pVVN and pVVN-P against Nef vaccinia infected or Nef peptide pulsed P815 targets. The CTL assay was performed using spleen cells harvested from immunized mice then in vitro stimulated prior to assay for chromium release from specific and non-specific vaccinia infected or peptide treated targets. Balb/C mice were immunized with 100 µg of pVVN, pVVN-P and control vector. Spleenocytes were obtained from the mice 2 weeks after the first and second boost and antigen specific CTL assay was performed in a 6 hr $^{51}$Cr release method. The specific lysis induced by spleenocytes from mice immunized with pVVN and pVVN-P was calculated and presented in FIG. 5. The graphs represent the percentage of specific lysis induced by subtracting the non specific lysis measured by assay using the target cells infected with control recombinant vaccinia. The CTL assay was performed on spleen cells harvested from immunized mice as described. Similar results were obtained in multiple experiments. At an effector: target ratio of 50:1 with Nef vaccinia infected targets, the percentage of specific lysis is 38 and 31% by spleenocytes from pVVN-P and pVVN immunized mice, respectively. The percentage of specific lysis was titratable. Similar results were observed with P815 targets expressing Vif. In repeated assays the percentage of specific lysis observed in mice immunized with pVVN-P appears reproducibly higher than the pVVN immunized mice.

Cytotoxic T cell lysis using HIV-1 infected targets: In general it has been difficult to perform CTL assays against HIV-1 viruses in the mouse system as HIV-1 does not naturally infect murine cells. In order to evaluate the ability of VVN and VVN-P to lyse HIV-1 infected targets, we constructed NIH3T3 cell lines expressing hCD4 and either CCR5 or Fusin co-receptors. NIH3T3 cell line was selected because of the MHC-compatability to Balb/C mice used in our study. Though murine cells do not support HIV-1 infection, these stable cell lines can be infected by different strains of HIV-1 for a single round of replication. We hypothesize that this single round of infection could be used for CTL assays. NIH3T3/hCD4/Fusin and NIH3T3/hCD4/CCR5 stable cell lines were infected with primary and well characterized laboratory viruses and the infectivity was measured by p24 antigen released into the medium (Table 2). Primary and molecular clones of HIV-1 isolates were able to infect these cell lines in detectable and reproducible fashion. Some primary isolates (92RW009 &BJ) did not infect these cells in a cell-free manner. In order to analyze, whether immunization of pVVN and pVVN-P constructs are able to kill HIV-1 infected target cells, we used clade B T-tropic (HIV-1 NL43) and dual-tropic (HIV-1 89.6) viruses to infect NIH3T3/CD4/CXCR4 and NIH3T3/CD4/CCR5 cells, respectively. These infected cells were used as target cells in this CTL assay. Spleenocytes from both pVVN and pVVN-P immunized mice induced lysis of the native pathogen infected cells. FIG. 6A shows data from experiments relating to Cytotoxic T lymphocyte response induced by pVVN and pVVN-P immunization against HIV-1 (T-tropic and dual-tropic) infected targets. NIH3T3 cells expressing CD4/CCR5 or CD4/CXCR4 were infected with dual-tropic (89.6) and T-tropic (NL43) viruses and used as target cells in CTL assay. Balb/C mice were immunized with 100 µg of pVVN, pVVN-P and control vector. Spleenocytes were obtained from the mice 2 weeks after the first and second boost and antigen specific CTL assay was performed in a 6 hr $^{51}$Cr release method. Natural (non specific) lysis of HIV-1 infected target cells was calculated and subtracted from the experimental samples to account for specific lysis induced by spleenocytes from immunized mice in this assay. Similar results were observed in multiple independent experiments. The data show the percentage of specific lysis by pVVN and pVVN-P using NIH3T3/CD4/CCR5 cells infected with HIV-1. At 50:1 effector: target ratio, the percentage of lysis by VVN and VVN-P is 29 and 42 respectively, in dual-tropic virus infected targets, whereas the specific lysis is 16 and 21% in T-tropic infected targets. Interestingly, the percentage of specific CTL induced by pVVN-P construct is always higher than pVVN construct immunization.

Figure 6B:
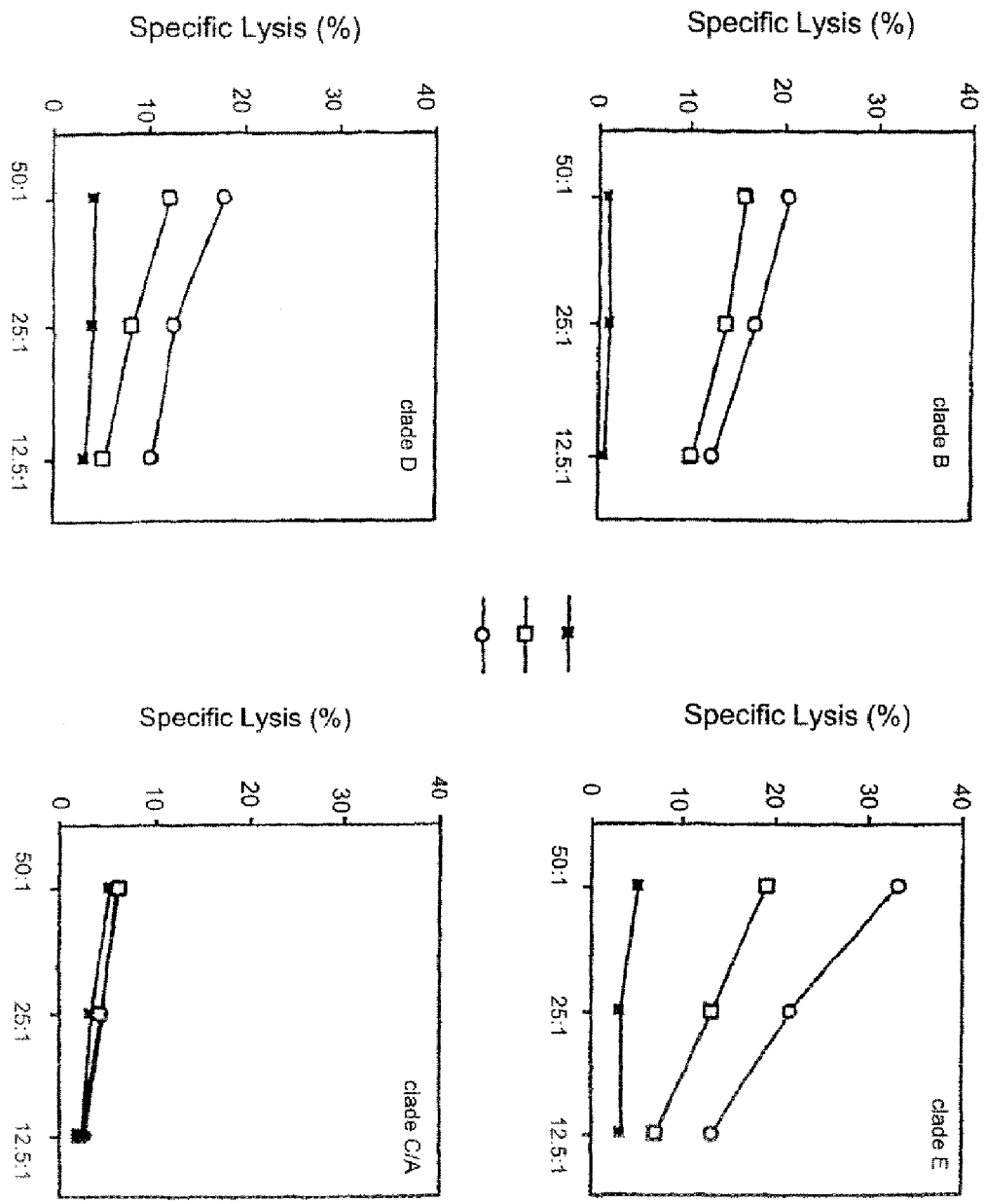

Cross clade CTL induced by pVVN and pVVN-P constructs: To evaluate the cross clade CTL recognition by these constructs (genes from B lade virus), we infected NIH3T3/hCD4/CCR5 or NIH3T3/hCD4/Fusin cell lines with HIV-1 isolates from clades D, E, C and A (Table 2). Once the cells reached moderate levels of infection, the cells were labeled with $^{51}$Cr and used as targets for the CTL assay. FIG. 6B shows data from experiments relating to cross clade CTL responses induced by spleenocytes isolated from mice immunized with VVN and VVN-P expression constructs. Cross lade CTL responses induced by spleenocytes isolated from mice immunized with VVN and VVN-P expression constructs: NIH3T3 cells expressing CD4/CCR5 or CD4/CXCR4 were infected with HIV-viruses derived from clades B, C/A, D and E were used as target cells in CTL assay. Balb/C mice were immunized with 100 µg of pVVN, pVVN-P and control vector. Spleenocytes were obtained from the mice 2 weeks after the first and second boost and antigen specific CTL assay was performed in a 6 hr $^{51}$Cr release method. Natural (non specific) lysis of HIV-1 infected target cells was calculated and subtracted from the experimental samples to account for specific lysis induced by spleenocytes from immunized mice in this assay. Similar results were observed in multiple independent experiments. The results presented in FIG. 6B show that both pVVN and pVVN-P induced CTL activity against lade B (clinical isolate), D (HIV-1$_{Zr6}$) and E (92THA022) infected targets. The activity titers with decreasing Effector: target ratio. Additionally, we have also noticed that spleenocytes from pVVN-P immunized mice induced higher CTL response against clade E and D infected targets then spleenocytes from pVVN immunized mice. However, we did not observe any CTL activity against clade C/A (92RW009) infected targets by both pVVN or pVVN-P immunization. It is not unlikely that this result reflects the lower infection rate of this isolate in these mouse cell lines (Table 2).

Discussion

Recent reports by UNAIDS show that globally over 36 million have been infected with HIV-1 and that this number is growing rapidly especially in developing countries. Though anti-viral therapies appear to control HIV-1 replication in vivo, their excessive cost and regimented administration protocol make them a less than ideal solution to the global HIV problem. Vaccines appear to be a most cost effective means to control HIV-1 infection worldwide. DNA vaccine technology represents an important tool in anti-viral vaccine development. The injection of DNA constructs containing parts of the HIV-1 genome as opposed to the whole genome can induce immunity without fear of infection. The generation of immune responses in vivo using DNA inoculation has been reported by different laboratories, including ours using different therapeutic targets and delivery techniques. Previously we and others have shown that a nucleic acid delivery approach produced anti-HIV-1 cellular and humoral immune responses in mice as well as in non-human primates and now in humans.

Arising data supports that induction of cell-mediated immunity may be an important feature for any candidate vaccine for HIV-1. During natural infection, anti-HIV-1 CTL responses appear very early and temporarily appear to correlate with the establishment of the viral set point. CTLs play a critical role in viral clearance by targeting and destroying virus-infected cells. Directing immune responses against viral proteins through the development of specific CTL responses would allow induction of a broader immune response against multiple antigenic targets within the virus. CTL activity against the virus is more commonly measured in healthy infected patients as compared to patients that have progressed to AIDS. Specific CTLs have been reported to decrease as disease pathogenesis increases establishing a link between CTL responses and preferred clinical status. Specific CTL responses appear to contribute to the maintenance of the asymptomatic phase of HIV-1 infection. Thus, the induction of strong HIV-1 specific CTLs iii vivo may play a crucial role in the ultimate protection of the host from the establishment of infection and ultimately to progression of HIV infection.

In this report we have evaluated the use of HIV-1 accessory genes vif, vpr, vpu and nef as immunogens. Once believed to be expendable, recent studies demonstrate that HIV-1 accessory genes may play an important role in AIDS pathogenesis by modulating normal cellular activity. For instance, cell free infection in primary cells can be enhanced by trans-complementing with a functional vif gene suggesting that Vif compliments viral replication in certain cell types (47). Both Vpu and Nef have been shown to be involved in the down regulation of CD4 and MHC-class I molecules when expressed internally. Nef blocks the expression of MHC-class 1 on the surface of infected cells thereby sheltering virally infected cells from CTL mediated destruction. Proper attenuation of the biological functions of these genes should eliminate any conceptual negative host cellular effects while maintaining their important immunological epitopes.

In our study, the vif, vpu and nef genes were cloned from viruses isolated from patients of varied clinical status. DNA constructs expressing both the functional and attenuated forms of these genes were analyzed for their ability to induce cellular and humoral responses in immunocompetent mice. The immunology data on use of the functional and attenuated genes as immunogens are quite comparable. Both attenuated as well as functional clones were able to induce a strong but variable CTL and T cell proliferation responses in mice. In general, the humoral response induced by these genes were at low levels most likely because these accessory genes are expressed intracellularly and therefore are not readily presented for B cell immunoglobin recognition. One important observation was that vpu can be used as an immunogen resulting antigen specific immune responses in these models.

HIV-1 accessory genes could be important immunogens for use in an anti-HIV DNA vaccine because they overall broaden the number of infected targets under immune attack thus helping to limit viral escape. Additionally, they may be under more selective pressure than the HIV-1 surface and core proteins. To evaluate this we adapted a novel system for testing cellular immune responses against HIV-1 clinical and laboratory isolates in mouse model. This single round infection system facilitates testing antigen abilities to generate effector responses against HIV-1 complete virus targets without the necessity of recombinant vector generation of individual viral antigens. This is supported by the demonstration here showing that mice immunized with pVVN and pVVN-P constructs were able to lyse targets derived from clades B, E and D of HIV-1. This suggest that because of the conservative nature of these accessory genes, they are able to induce cross lade CTL response which may be a useful additional tool in vaccine development. Additionally, in this study we have also shown the feasibility of using of pathogenic genes in attenuated forms. Our initial analysis using the accessory genes as vaccine targets show that these constructs were well tolerated in mice and did not show any adverse effects. A clear benefit demonstrated here is the ability of accessory genes to participate in cross lade recognition and CTL responses. It appears that insertion of proteolytic cleavage sites results in more natural processing of such fused vaccine antigens and this may add additional value to these approaches, as is evidenced here by the observation of the trend towards higher cellular immune responses induced by these cassettes. Such responses are likely to be important for vaccine consideration.

Combining the accessory genes as part of a multicomponent vaccine cocktail that includes the structural and enzymatic genes might induce a more vigorous immune response in the infected individuals as a therapeutic vaccine. Such an approach could be an interesting supplement to new standard anti retroviral therapeutic regimes, thus increasing the number of gene targets under therapeutic attack. Seminal studies on the development of live attenuated SIV vaccines have demonstrated the importance of HIV-1 accessory genes as in vivo contributors to viral pathogenesis. In theory CTL responses that select for viral escape mutants that lack accessory gene functions would be expected to result in in vivo viral phenotypes that are now attenuated. Thus even a non sterilizing prophylactic vaccine or in a therapeutic setting as immune therapy outcome would still be expected to have two specific benefits. One benefit is that the resulting viruses could loose aspects of pathogenesis and the second is that the remaining virus could actually mimic aspects of live attenuated vaccine protection. A single DNA vaccine construct, as we have made, that can induce immunity to numerous genes may be easier to administer and more cost effective than developing and administering single gene DNA vaccine cassettes.

TABLE 1

Biological assays used in the study to identify attenuated vif, vpu, vpr and nef HIV-1 accessory genes.

| Genes Used | Biology | Mutation |
|---|---|---|
| Vif (N17) | Lack of transcomplementation of vif HIV-1 provirus in cell-free infection | Mutations at amino acid 26, 31, 36, 45, 60, 127, 136, 140 and 150. |

TABLE 1-continued

Biological assays used in the study to identify attenuated vif, vpu, vpr and nef HIV-1 accessory genes.

| Genes Used | Biology | Mutation |
|---|---|---|
| Vpr (NA) | Inhibition of T cell proliferation & Cyokine synthesis | ND |
| Vpu (5256) | Loss of CD4 and MHC-I degradation | Mutations at amino acid 52 and 56 |
| Nef (S313) | Loss of down regulation of CD4 and MHC-I expression | Mutations at amino acid 2, 10, 11, 14, 15, 19, 21-26, 55, 106, 113, 131, 164, 174, 185, 191, 199, 201 and 213. |

HIV-1 accessory genes vif and Nef were cloned from clinical isolates and characterised based on their functional assay. Mutations were introduced in Vpr and Vpu based on earlier studies (41, 58) NA, not applicable.

TABLE 2

Infectivity of NIH3T3 cells expressing human CD4 and CCR5 or CD4 and CXCR4 by HIV-1 viral isolates from various clades with different cellular tropism.

| Cell Lines Used | Virus used for infection | Clade | Cellular tropism | p24 antigen production (ng/ml) |
|---|---|---|---|---|
| NIH3T3/CD4/CXCR4 | PNL43 | B | T-tropic | 110899.0 |
| NIH3T3/CD4/CXCR4 | Z6 | D | T-tropic | 22815.46 |
| NIH3T3/CD4/CXCR4 | KS (clinical) | B | T-tropic | 22311.9 |
| NIH3T3/CD4/CCR5 | 89.6 | B | Dual tropic | 89254.7 |
| NIH3T3/CD4/CXCR4 | 92THA022 | E | ND | 32417.6 |
| NIH3T3/DD4/CXCR4 | 92RW009 - | C/A | T-tropic | 256.06 |

HIV-1 primary isolates were obtained from UNAIDS through NIH AIDS RRRP and propagated in normal PBMCs. NIH 3T3 cells expressing hCD4/CCR5 and hCD4/CXCR4 were infected with 10-50 ng of p24 antigen equivalent of virus for 12 hrs. Cells were washed twice with PBS and maintained in normal culture medium. Cells were monitored for infection and the cells and the medium were collected and assayed for p24 production, ND, Not determined.

The invention claimed is:

1. A nucleic acid molecule comprising a coding sequence encoding a polyprotein comprising HIV Vif, HIV Vpu and HIV Nef.

2. The nucleic acid molecule of claim 1 wherein said coding sequence operably linked to regulatory elements.

3. The nucleic acid molecule of claim 1 wherein said nucleic acid molecule is a plasmid.

4. A plasmid of claim 3 wherein said coding sequence is operably linked to regulatory elements.

5. The nucleic acid molecule of claim 1 wherein HIV Vif is SEQ ID NO:1.

6. The nucleic acid molecule of claim 1 wherein HIV Vpu is SEQ ID NO:2.

7. The nucleic acid molecule of claim 1 wherein HIV Nef is SEQ ID NO:3.

8. The nucleic acid molecule of claim 1 wherein the polypeptide encoded by the coding sequence comprises HIV Vif, HIV Vpu and HIV Nef in the order HIV Vif, HIV Vpu and HIV Nef relative to each other from N terminal to C terminal.

9. The nucleic acid molecule of claim 8 wherein said polypeptide encoded by the coding sequence has a protease cleavage site is located in between HIV Vif, and HIV Vpu and a protease cleavage site is located in between HIV Vpu and HIV Nef.

10. The nucleic acid molecule of claim 9 wherein HIV Vif is SEQ ID NO:1.

11. The nucleic acid molecule of claim 9 wherein HIV Vpu is SEQ ID NO:2.

12. The nucleic acid molecule of claim 9 wherein HIV Nef is SEQ ID NO:3.

13. The nucleic acid molecule of claim 9 wherein the protease cleavage site is REKRAVVG (SEQ ID NO:4).

14. The nucleic acid molecule of claim 1 wherein HIV Vif is SEQ ID NO:1; HIV Vpu is SEQ ID NO:2 and HIV Nef is SEQ ID NO:3.

* * * * *

UNITED STATES PATENT AND TRADEMARK OFFICE
CERTIFICATE OF CORRECTION

| | | |
|---|---|---|
| PATENT NO. | : 7,488,484 B2 | Page 1 of 1 |
| APPLICATION NO. | : 10/312197 | |
| DATED | : February 10, 2009 | |
| INVENTOR(S) | : David B. Weiner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1457 days.

Signed and Sealed this

Nineteenth Day of October, 2010

David J. Kappos
*Director of the United States Patent and Trademark Office*